US012558510B2

(12) United States Patent
Lau et al.

(10) Patent No.: US 12,558,510 B2
(45) Date of Patent: Feb. 24, 2026

(54) APPARATUS FOR USE IN A RESPIRATORY SUPPORT SYSTEM

(71) Applicant: Fisher & Paykel Healthcare Limited, Auckland (NZ)

(72) Inventors: Andrew Chi Lup Lau, Auckland (NZ); Jason Allan Klenner, Auckland (NZ); Mark Thomas O'Connor, Auckland (NZ); Kevin Blake Powell, Auckland (NZ); Brent Ian Laing, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1240 days.

(21) Appl. No.: 17/268,216

(22) PCT Filed: Aug. 13, 2019

(86) PCT No.: PCT/IB2019/056854
§ 371 (c)(1),
(2) Date: Feb. 12, 2021

(87) PCT Pub. No.: WO2020/035783
PCT Pub. Date: Feb. 20, 2020

(65) Prior Publication Data
US 2021/0338962 A1        Nov. 4, 2021

Related U.S. Application Data

(60) Provisional application No. 62/718,372, filed on Aug. 13, 2018.

(51) Int. Cl.
A61M 16/08        (2006.01)
A61M 16/00        (2006.01)
(Continued)

(52) U.S. Cl.
CPC .... *A61M 16/0816* (2013.01); *A61M 16/0875* (2013.01); *A61M 39/1011* (2013.01);
(Continued)

(58) Field of Classification Search
CPC .......... A61M 16/0816; A61M 16/0875; A61M 16/0672; A61M 16/1095; A61M 39/1011; A61M 39/105; A61M 2205/0216
See application file for complete search history.

(56) References Cited

U.S. PATENT DOCUMENTS 1,542,335 A        6/1925 Emilio
2,302,707 A        11/1942 Gustave
(Continued)

FOREIGN PATENT DOCUMENTS

AU        2013257505        12/2013
CN        2207505        7/1995
(Continued)

OTHER PUBLICATIONS

Patent Cooperation Treaty, International Search Report and Written Opinion, Application No. PCT/IB2019/056854, dated Nov. 28, 2019, in 22 pages.
(Continued)

*Primary Examiner* — Patrick C Williams
(74) *Attorney, Agent, or Firm* — VIA LLP

(57) ABSTRACT

This invention relates to a connector for a component of a medical breathing circuit. The connector comprises an inner body and an outer body. The inner body and the outer body being separate components. The inner body having a retention mechanism configured to engage another connector, and an outer body configured to at least partly surround the inner body, the outer body having a tube engagement mechanism.

15 Claims, 24 Drawing Sheets

(51) Int. Cl.

| | |
|---|---|
| *A61M 16/06* | (2006.01) |
| *A61M 16/10* | (2006.01) |
| *A61M 39/10* | (2006.01) |

(52) U.S. Cl.

CPC ....... *A61M 39/105* (2013.01); *A61M 16/0066*
(2013.01); *A61M 16/0666* (2013.01); *A61M*
*16/109* (2014.02); *A61M 2205/0216* (2013.01)

(56) References Cited

U.S. PATENT DOCUMENTS

| | | | |
|---|---|---|---|
| 3,826,523 | A | 7/1974 | Eschbaugh |
| 3,990,727 | A | 11/1976 | Gallagher |
| 4,177,945 | A | 12/1979 | Schwartz et al. |
| 4,188,081 | A * | 2/1980 | Holden ................ H01R 13/005 |
| | | | 439/192 |
| 4,458,719 | A | 7/1984 | Strybel |
| 4,541,658 | A | 9/1985 | Bartholomez |
| 4,653,542 | A | 3/1987 | Tascher |
| 4,714,279 | A * | 12/1987 | Custeau .............. F01N 13/1805 |
| | | | 285/251 |
| 4,844,512 | A | 7/1989 | Gahwiler |
| 4,941,689 | A | 7/1990 | Sjoberg |
| 4,967,744 | A | 11/1990 | Chua |
| 5,447,337 | A | 9/1995 | Ruckwardt |
| 5,640,951 | A | 6/1997 | Huddart et al. |
| 5,794,986 | A | 8/1998 | Gansel et al. |
| 6,050,260 | A | 4/2000 | Daniell et al. |
| 6,401,713 | B1 | 6/2002 | Hill et al. |
| 6,415,789 | B1 | 7/2002 | Freitas et al. |
| 6,907,882 | B2 | 6/2005 | Ging et al. |
| 6,953,354 | B2 | 10/2005 | Edirisuriya et al. |
| 7,354,079 | B2 | 4/2008 | Rehder et al. |
| 7,390,028 | B2 | 6/2008 | Blazek et al. |
| 7,637,288 | B2 | 12/2009 | Kressierer/Huber et al. |
| 7,918,243 | B2 | 4/2011 | Diodati et al. |
| 8,733,349 | B2 | 5/2014 | Bath et al. |
| 8,770,190 | B2 | 7/2014 | Doherty et al. |
| 9,132,252 | B2 | 9/2015 | Barlow et al. |
| 9,248,248 | B2 | 2/2016 | Virr et al. |
| 9,533,117 | B2 | 1/2017 | Gray |
| 9,784,387 | B2 | 10/2017 | Kaye et al. |
| 9,808,612 | B2 | 11/2017 | Gulliver et al. |
| 9,814,856 | B2 | 11/2017 | Payton et al. |
| D809,656 | S | 2/2018 | Lau et al. |
| 10,058,666 | B2 | 8/2018 | Kwok et al. |
| D857,880 | S | 8/2019 | Lau et al. |
| 10,675,429 | B2 | 6/2020 | Ging et al. |
| 10,907,637 | B2 | 2/2021 | Row et al. |
| 2003/0196662 | A1 | 10/2003 | Ging et al. |
| 2003/0236015 | A1 | 12/2003 | Edirisuriya et al. |
| 2007/0025811 | A1 | 2/2007 | Wilhelm |
| 2008/0264413 | A1 | 10/2008 | Doherty et al. |
| 2010/0116272 | A1 | 5/2010 | Row et al. |
| 2010/0236552 | A1 | 9/2010 | Kwok et al. |
| 2011/0067704 | A1 | 3/2011 | Kooij et al. |
| 2013/0019867 | A1 | 1/2013 | Mashak |
| 2014/0150798 | A1 | 6/2014 | Fong et al. |
| 2015/0157825 | A1 | 6/2015 | Chang |
| 2015/0258324 | A1 | 9/2015 | Chida et al. |
| 2015/0320960 | A1 | 11/2015 | Barlow et al. |
| 2016/0310689 | A1 | 10/2016 | Osborne et al. |
| 2016/0325067 | A1 | 11/2016 | Harwood et al. |
| 2017/0333663 | A1 | 11/2017 | Huber et al. |
| 2017/0368291 | A1 | 12/2017 | Heatherington et al. |
| 2018/0043125 | A1 | 2/2018 | Bencke et al. |
| 2018/0289910 | A1 | 10/2018 | Flower et al. |
| 2018/0311457 | A1 | 11/2018 | Kavermann |
| 2019/0001091 | A1 | 1/2019 | Bath et al. |
| 2019/0022344 | A1 | 1/2019 | Lau et al. |
| 2019/0351173 | A1 | 11/2019 | Dantanarayana et al. |

FOREIGN PATENT DOCUMENTS

| | | |
|---|---|---|
| CN | 102686266 | 9/2012 |
| CN | 103182127 | 7/2013 |
| CN | 103857432 | 6/2014 |
| CN | 104487122 A | 4/2015 |
| CN | 105813679 A | 7/2016 |
| CN | 205411878 | 8/2016 |
| CN | 106232167 | 12/2016 |
| CN | 108025156 | 5/2018 |
| CN | 108136150 A | 6/2018 |
| DE | 10229004 | 1/2004 |
| DE | 102008061415 | 6/2010 |
| EP | 0928620 | 7/1999 |
| EP | 1197237 | 4/2002 |
| EP | 1741462 | 1/2007 |
| EP | 2465564 | 6/2012 |
| EP | 2469146 | 6/2012 |
| EP | 2954918 | 12/2015 |
| EP | 2992921 | 3/2016 |
| GB | 2323418 A | 5/1997 |
| GB | 2323418 | 9/1998 |
| GB | 2451891 | 2/2009 |
| WO | WO 94/23236 | 10/1994 |
| WO | WO 00/66207 | 11/2000 |
| WO | WO 03/072175 | 9/2003 |
| WO | WO 2007/009182 | 1/2007 |
| WO | WO 2011/056080 | 5/2011 |
| WO | WO 2013/002655 | 1/2013 |
| WO | WO 2013/022356 | 2/2013 |
| WO | WO 2014/025266 | 2/2014 |
| WO | WO 2014/144732 | 3/2014 |
| WO | WO 2014/129911 | 8/2014 |
| WO | WO 2014/205513 | 12/2014 |

OTHER PUBLICATIONS

Medical Products Catalogue, Apr. 1988-Mar. 1989.

* cited by examiner

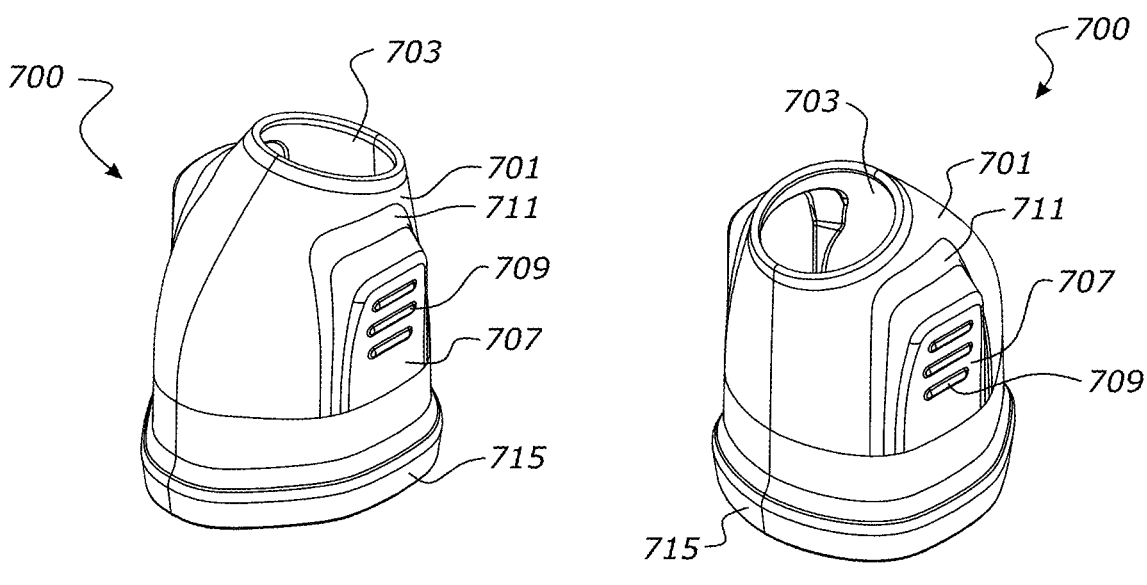
FIG. 6A                    FIG. 6B
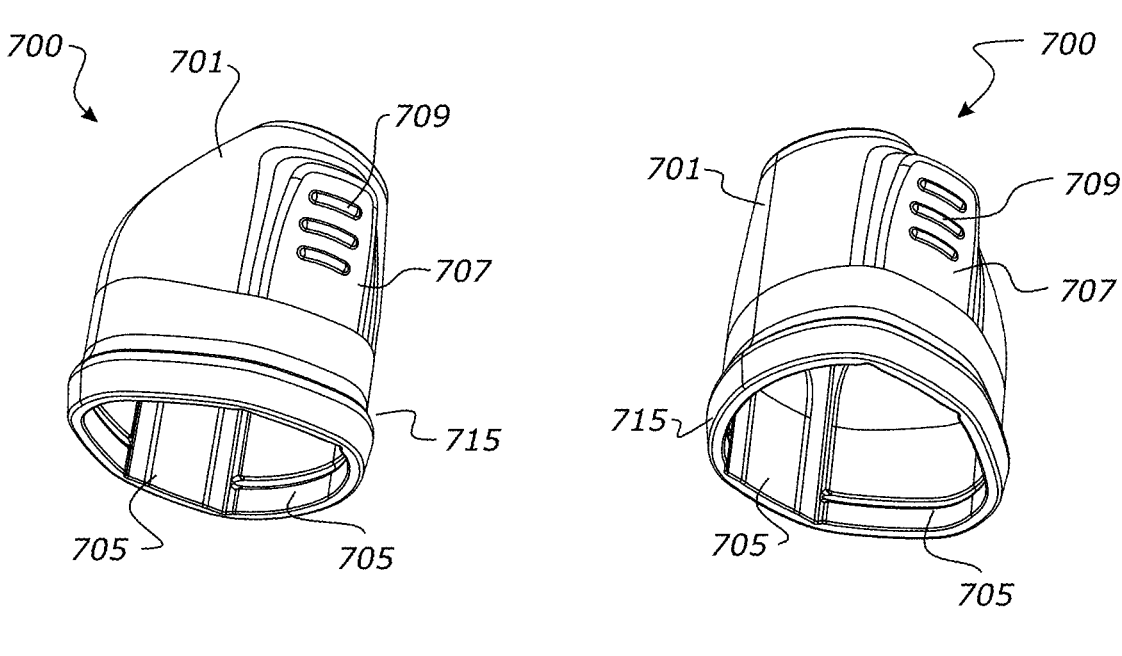
FIG. 6C                    FIG. 6D

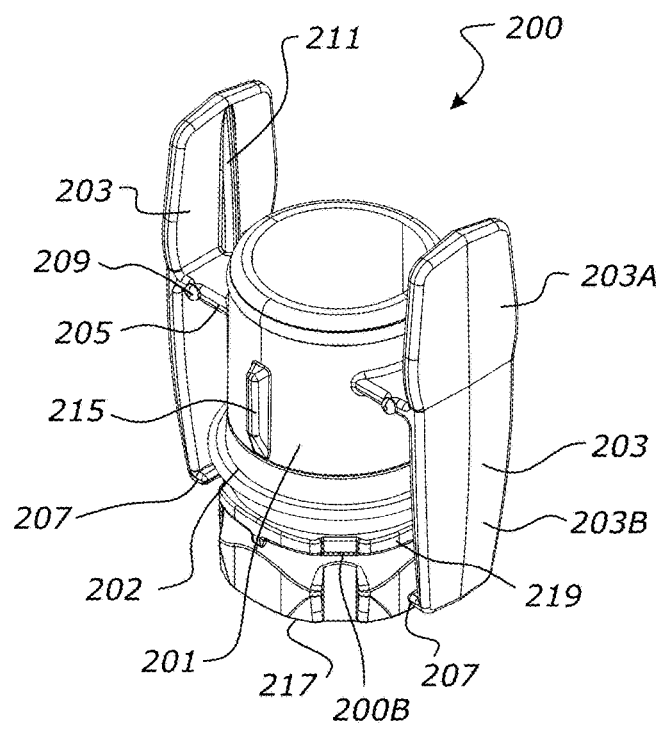
FIG. 7
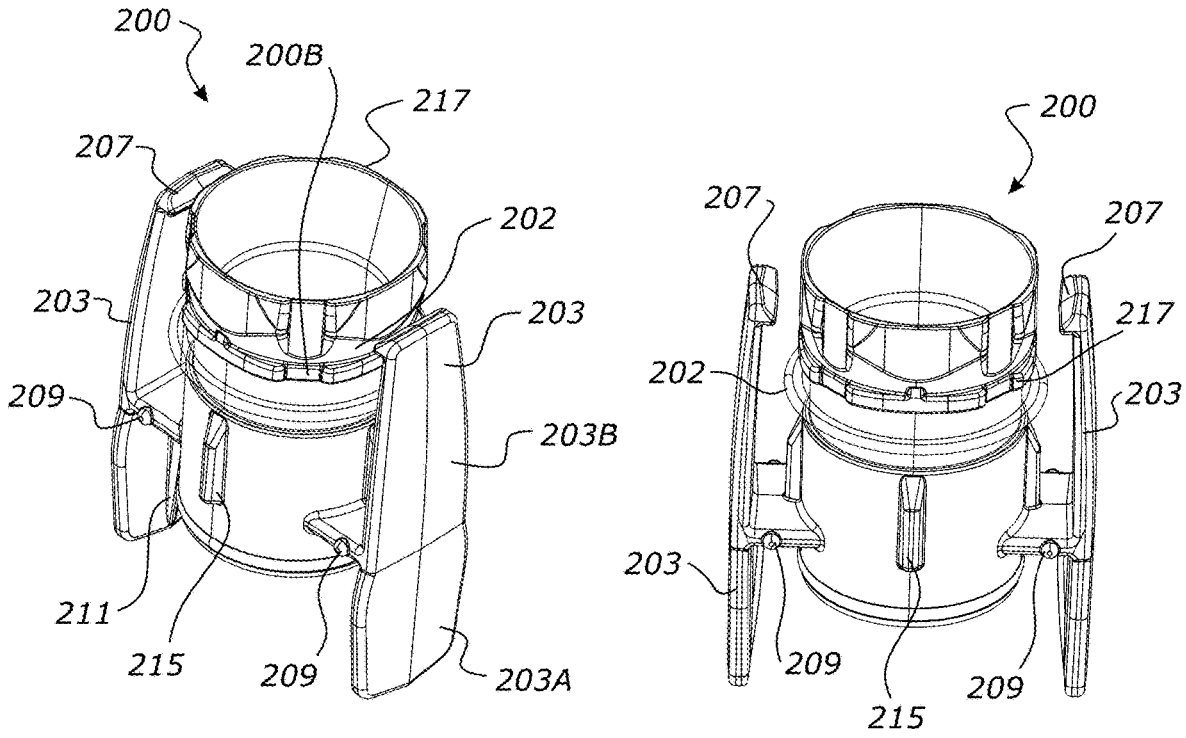
FIG. 8                    FIG. 9

*400*

*407*

*300*

*407*

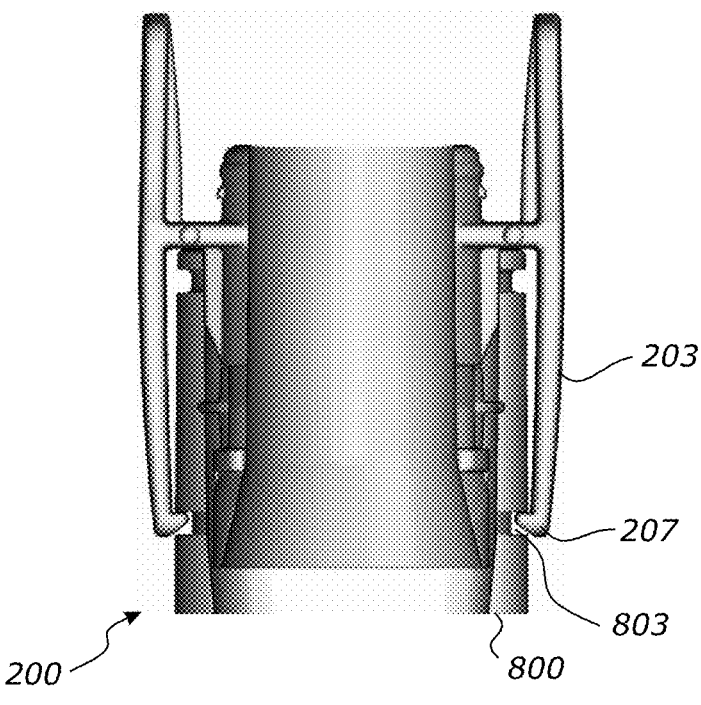
*203*
*207*
*803*
*200*
*800*
FIG. 22
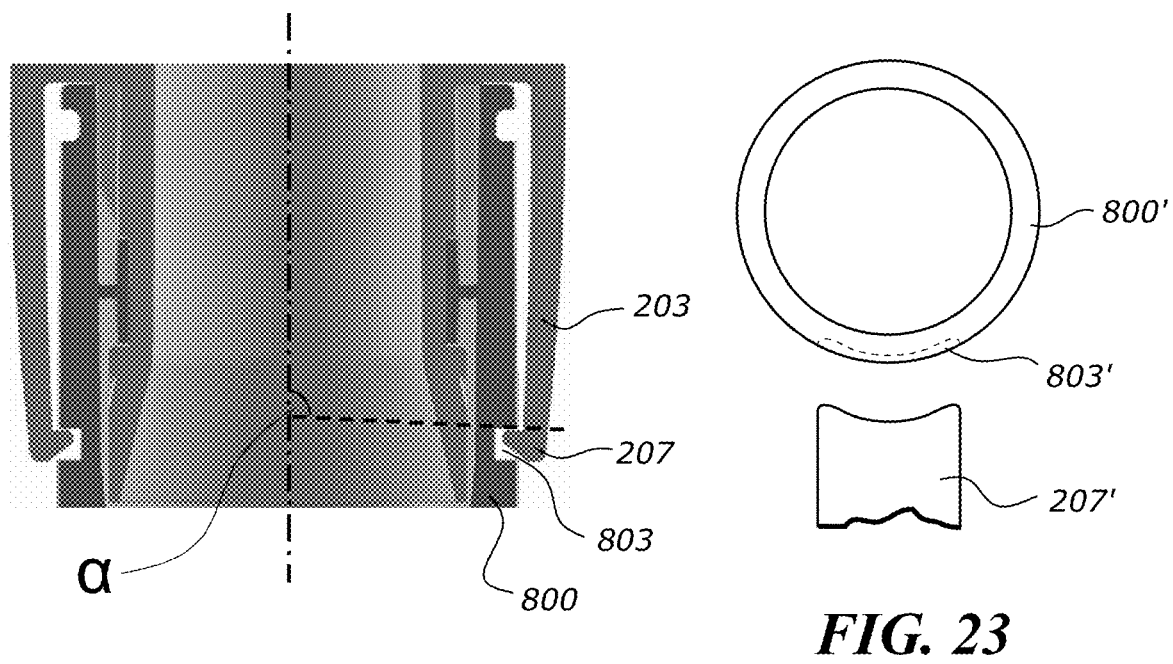
*203*
*207*
*803*
*α*
*800*
*800'*
*803'*
*207'*
FIG. 22A
FIG. 23

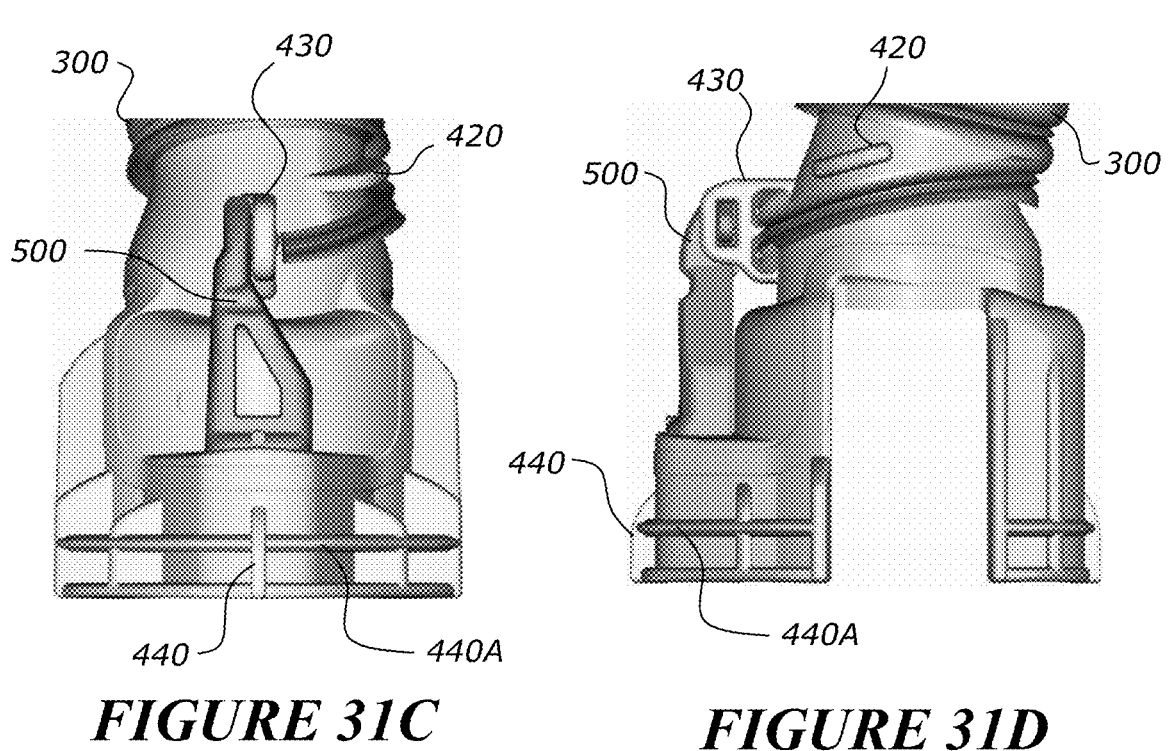
FIGURE 31C          FIGURE 31D
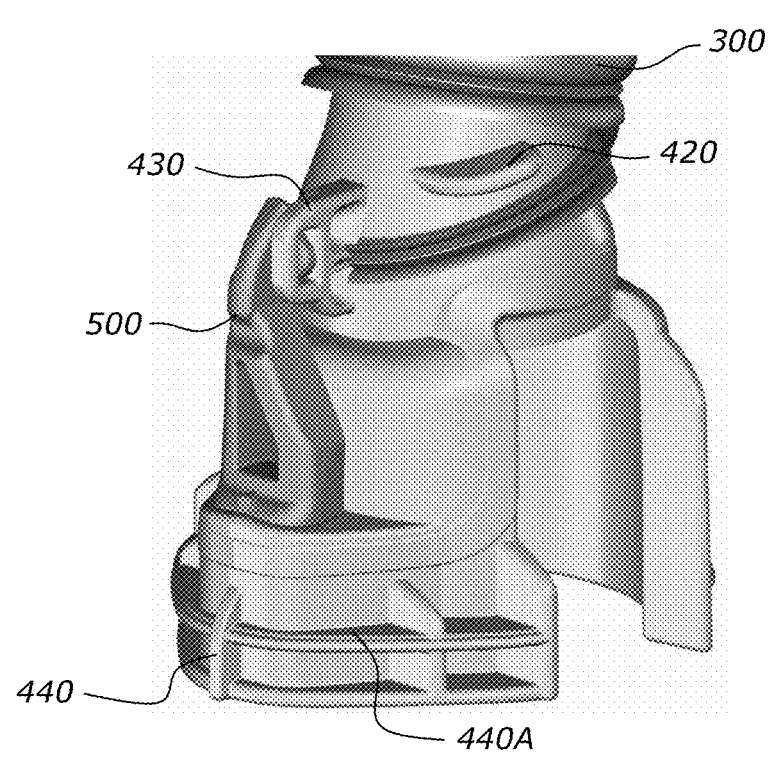
FIGURE 31E

APPARATUS FOR USE IN A RESPIRATORY SUPPORT SYSTEM

TECHNICAL FIELD

The present disclosure generally relates to a connector to be provided at a terminal end of a conduit. More particularly, the present disclosure relates to a releasable, yet secure, connector to be provided at the terminal end of a medical breathing conduit forming a part of a medical breathing circuit, for a releasable, yet secure, connection to be made between an end of the conduit with another device of the circuit (e.g. a humidifier or a flow generator or another conduit).

BACKGROUND

Alternative forms of connectors at the end of a conduit, such as a medical breathing conduit, for a connection to be made with a device forming a part of a breathing circuit, such as a medical breathing circuit, are desirable.

In particular, provision of such connectors which provide for a releasable yet secure connection facilitate particular advantages. For example, a secure connection between the terminal end of a conduit and a device (such as a humidifier or a flow generator, such as a blower), or between two conduits, gives an operator or user (and the patient) reassurance of the delivery of a desired or intended respiratory therapy.

SUMMARY

It is an object of certain embodiments disclosed herein to provide a connector for use in a medical breathing circuit or respiratory support system that will at least go some way towards improving on the above or which will at least provide the public or the medical profession with a useful choice.

In a first aspect, there is provided a connector for a component of a medical breathing circuit, the connector comprising: an inner body and an outer body, the inner body and the outer body being separate components; the inner body having a retention mechanism configured to engage another connector; and an outer body configured to at least partly surround the inner body, the outer body having a tube engagement mechanism.

In one embodiment, the inner body further comprises a sealing mechanism configured to provide a seal between the inner body and the other connector.

In one embodiment, at least part of the inner body comprises a first material and at least part of the outer body comprises a second material.

In one embodiment, the first material is stiffer than the second material.

In one embodiment, the retention mechanism of the inner body comprises a flexing region comprising the first material.

In one embodiment, the retention mechanism comprises a lever that is movable relative to the body about the flexing region.

In one embodiment, the lever has a retention portion on one side of the flexing region and an actuation portion on the other side of the flexing region.

In one embodiment, the lever has a retention portion on one portion of the flexing region and an actuation portion on another portion of the flexing region.

In one embodiment, the retention portion of the or each lever comprises the first material.

In one embodiment, the actuation portion of the or each lever comprises the first material.

In one embodiment, the entire retention mechanism comprises the first material.

In one embodiment, the retention mechanism comprises two levers.

In one embodiment, the distance between the retention portions of the two levers in a disengaged configuration is equal to or less than the distance in an engaged configuration.

In one embodiment, the distance between the retention portions of the two levers in an engaged configuration is the same as the distance in the disengaged configuration.

In one embodiment, the outer body has cut-outs to allow a portion of the inner body to sit within the outer body and a portion of the inner body to sit outside the outer body.

In one embodiment, the portion of the inner body to sit outside the outer body is the retention mechanism.

In one embodiment, the flexing region is provided by a bridge.

In one embodiment, the bridge has features to align the bridge with the outer body.

In one embodiment, the features are alignment bosses.

In one embodiment, the bridge is arranged between the actuation portion and the retention portion.

In one embodiment, the bridge comprises a strengthening feature.

In one embodiment, the strengthening feature comprises a step at an intersection between the actuation portion and the bridge.

In one embodiment, the strengthening feature comprises two steps extending towards each other from opposing sides of the lever towards a central plane of the bridge.

In one embodiment, the strengthening feature comprises a thickened portion of the bridge.

In one embodiment, the thickened portion is provided at an intersection of the actuation portion and the bridge.

In one embodiment, the actuation portion comprises a rib that limits flexing of the actuation portion.

In one embodiment, the entire inner body comprises the first material.

In one embodiment, the first material has a higher Young's modulus than the second material.

In one embodiment, the second material comprises polyolefins.

In one embodiment, the second material comprises polypropylene.

In one embodiment, the first material comprises polyoxymethylene.

In one embodiment, the lumen of the inner body and the lumen of the outer body are substantially aligned.

In one embodiment, the lumen of the inner body and the lumen of the outer body are coaxial.

In one embodiment, the connector further comprises an inner body and outer body sealing mechanism configured to seal the inner body and the outer body together; and an inner body and outer body retention mechanism configured to retain the inner body and the outer body together, the inner body and outer body sealing mechanism and retention mechanism being separate mechanisms.

In one embodiment, the inner body and outer body sealing mechanism is additionally configured to retain the inner body and the outer body together.

In one embodiment, the inner body and outer body sealing mechanism comprises a protrusion. Optionally, the sealing mechanism is an annular sealing protrusion.

In one embodiment, the inner body and outer body sealing mechanism comprises a complementary recess.

In one embodiment, the inner body comprises the protrusion and the outer body comprises the recess. In one embodiment, the annular sealing protrusion comprises an angled cross-sectional profile.

In one embodiment, the annular sealing protrusion is provided on an external surface of the inner body and is configured to be in interference fit with an inner surface of the outer body.

In one embodiment, the inner body and outer body retention mechanism comprises a protrusion, preferably a barb.

In one embodiment, the inner body and outer body retention mechanism comprises a complementary indentation or aperture.

In one embodiment, the complementary indentation or aperture is defined by one or more walls, and the or each barb is positioned in the complementary indentation or aperture without abutting the one or more walls.

In one embodiment, the inner body and outer body retention mechanism protrusion is an annular protrusion, being an annular retention protrusion.

In one embodiment, the protrusion comprises an angled cross-sectional profile.

In one embodiment, the annular retention protrusion has a rounded cross-sectional profile.

In one embodiment, the protrusion is configured to be interference fit with an inner surface of the outer body.

In one embodiment, the complementary indentation or aperture is an annular indentation or aperture.

In one embodiment, the inner body and outer body retention mechanism protrusion comprises a complementary indentation or aperture, and wherein the complementary indentation or aperture is an annular indentation, aperture or recess.

In one embodiment, the annular sealing protrusion and annular retention protrusion have different diameters.

In one embodiment, the annular sealing protrusion and annular retention protrusion have different cross-sectional profiles.

In one embodiment, the annular retention protrusion has a rounded cross-sectional profile.

In one embodiment, the annular retention protrusion has an angled cross-sectional profile.

In one embodiment, the inner body and outer body sealing mechanism comprises an interference fit between a tapered wall of the inner body and a complementary tapered wall of the outer body.

In one embodiment, a terminal end of the inner body extends beyond an end of the outer body.

In one embodiment, the terminal end has a greater diameter than the remainder of the inner body.

In one embodiment the inner body comprises a wall that tapers outwardly towards the terminal end.

In one embodiment a diameter of an inner wall of the inner body at the terminal end is greater than the diameter of a remainder of the inner wall.

In one embodiment the inner walls of the terminal end form a smooth/continuous profile with the inner walls of the inner body.

In one embodiment, the inner body is provided as a separate component that is independent of a tube or devoid of tube connection features.

In one embodiment, the outer body is provided with the tube connection features and the inner body is devoid of tube connection features.

In one embodiment, the inner body excludes tube connection features.

In one embodiment, the outer body comprises the tube connection features, such that, when an assembly of the inner body and the outer body is made said assembly is connected to the tube via tube connection features of the outer body only.

In accordance with another aspect, there is provided a combination of a connector as described above together with a second connector and a tube, the second connector having an internal passage, wherein the inner body is at least partly located in the internal passage of the second connector and the retention mechanism is engaged with the second connector, and the tube engagement mechanism is engaged with the tube.

In one embodiment, the second connector has one or more recesses and the retention mechanism is engaged with the one or more recesses.

In one embodiment, there is provided the combination together with a second connector, the second connector having an internal passage, wherein the inner body is at least partly located in the internal passage of the second connector such that the sealing mechanism substantially seals with the internal passage and the retention mechanism engages with the exterior of the second connector.

In one embodiment, there is provided the combination together with a second connector, the second connector having an internal passage, wherein, when the connector is connected with the second connector and the tube, the inner body is at least partly located in the internal passage of the second connector such that the sealing mechanism substantially seals with the internal passage and the retention mechanism engages with the exterior of the second connector.

A connector for a component of a medical breathing circuit, the connector comprising: a body defining a gases pathway, the body having a retention mechanism with an actuation feature that is manually operable; and a flexible elastomeric cover configured to extend over the actuation feature while allowing the actuation feature to be manually operated.

A connector for a component of a medical breathing circuit, the connector comprising: a body defining a gases pathway, the body having a retention mechanism with an actuation feature that is manually operable; and a flexible elastomeric cover configured to extend over the actuation feature and comprising at least one thickened portion and at least one thinned portion to allow the actuation feature to be manually operated.

In one embodiment, the retention mechanism is a lever that is movable relative to the body about a flexing portion or a pivot.

In one embodiment, the lever has a retention portion on one side of the flexing portion or pivot and an actuation portion on the other side of the flexing portion or pivot.

In one embodiment, the elastomeric cover has a thickened portion that corresponds to the actuation portion.

In one embodiment, the thickened portion is shaped to conform to an external shape of the actuation portion.

In one embodiment, the thickened portion has an external surface feature.

In one embodiment, the elastomeric cover has a thinned portion connecting the thickened portion to the rest of the elastomeric cover.

In one embodiment, the elastomeric cover has a base with a thickened shoulder.

In one embodiment, the elastomeric cover has a thickened shoulder proximate the retention portion.

In one embodiment, the elastomeric cover is friction or interference fitted with the body.

In one embodiment, the body is formed of rigid plastic.

In one embodiment, the elastomeric cover comprises a shape that substantially conforms to the external shape of the body.

In one embodiment, the elastomeric cover keys with the body.

In one embodiment, the elastomeric cover has a recess to engage a complementary flange in the body.

In one embodiment, the body has one or more ribs to support the cover.

In one embodiment, the connector further comprises at least one electrical contact.

In one embodiment, the body has material to pneumatically seal about the electrical connection.

In one embodiment, the material has ribs to support the cover.

In accordance with another aspect, there is provided a combination of a connector as described above together with a second connector, wherein the retention mechanism is engaged with the second connector.

In accordance with another aspect, there is provided a combination of a connector as described above together with a second connector, wherein, when the connector is connected with the second connector and the tube, the retention mechanism is engaged with the second connector.

In one embodiment, the second connector has one or more recesses and the retention mechanism is engaged with the one or more recesses.

In one embodiment, the combination further comprises a tube, wherein the connector comprises a tube engagement mechanism, and the tube engagement mechanism is engaged with the tube.

In accordance with another aspect, there is provided a connector for a component of a medical breathing circuit, the connector comprising: a body defining a gases pathway, and having an outwardly extending protrusion; and a sealing member located between the outwardly extending protrusion and a terminal end of the body.

In one embodiment, the sealing member is spaced at a distance from the terminal end.

In one embodiment, the gases pathway is defined by an inner wall that tapers outwardly towards the terminal end.

In one embodiment, the body has an outer wall that tapers outwardly towards the terminal end.

In one embodiment, the diameter of the inner and/or outer wall of the terminal end is greater than the diameter of the rest of the body.

In one embodiment, the body has an assembly guide extending from the terminal end towards the sealing member.

In one embodiment, the body has a shoulder between the sealing member and the terminal end.

In one embodiment, the protrusions extend in a direction that is generally parallel to the longitudinal axis of the body.

In one embodiment, the body comprises a plurality of outwardly extending protrusions.

In one embodiment, one or more of the plurality of outwardly extending protrusions has an angled or tapered end to act as an alignment guide.

In accordance with another aspect, there is provided a connector for a component of a medical breathing circuit, the connector configured to connect a second connector having an internal passage, the connector comprising: a body configured to be at least partly located in the internal passage of the second connector, the body having a sealing mechanism to seal with the internal passage and a retention mechanism to engage with the exterior of the second connector.

In accordance with another aspect, there is provided a connector for a component of a medical breathing circuit, the connector configured to connect a second connector having an internal passage, the connector comprising: a body comprising a gas flow passage and configured to be at least partly located in the internal passage of the second connector, the body having a sealing mechanism to seal with the internal passage and a retention mechanism to engage with the exterior of the second connector, wherein the retention mechanism comprises a lever that is movable relative to the body about a flexing region, and wherein the lever has a retention portion on one side of the flexing region and an actuation portion on the other side of the flexing region.

In one embodiment, the sealing mechanism comprises a sealing member.

In one embodiment, the sealing member is, or comprises, a wiper seal.

In one embodiment, the sealing member is, or comprises, an O-ring.

In one embodiment, the body has a recess for receiving the sealing member.

In one embodiment, the sealing member has an at-rest outer diameter, the at-rest outer diameter of the sealing member being larger than an inner diameter of the internal passage with which it seals.

In one embodiment, the retention mechanism comprises a lever that is movable relative to the body about a flexing region.

In one embodiment, wherein the lever has a retention portion on one side of the flexing region and an actuation portion on the other side of the flexing region.

In one embodiment, the retention portion comprises a protrusion extending towards a centre of the connector.

In one embodiment, the protrusion is angled relative to a central axis extending through the centre of the connector.

In one embodiment, the protrusion is angled at about 85° to about 115°, more preferably about 90° to about 110°, even more preferably about 93° to about 102°, most preferably may be about 95° to about 99°.

In one embodiment, wherein the flexing region is provided by a bridge.

In one embodiment, wherein the retention mechanism comprises two levers.

In one embodiment, movement of the actuation portion towards the centre of the connector causes movement of the retention mechanism to move away from the centre of the connector.

In one embodiment, the distance between the retention portions of the two levers in the disengaged configuration is equal to or less than the distance in the engaged configuration.

In one embodiment, the distance between the retention portions of the two levers in the disengaged configuration is the same as the distance in the engaged configuration.

In one embodiment, the body is an inner body, and the connector further comprises an outer body, the outer body having cut-outs to allow a portion of the inner body to sit within the outer body and a portion of the inner body to sit outside the outer body.

In one embodiment, the body is an inner body, and the connector further comprises an outer body.

In one embodiment, a portion of the inner body sits inside the outer body and the retention mechanism sits outside the outer body.

In one embodiment, the bridge has features to align the bridge with the cut-outs.

In one embodiment, the features are alignment bosses.

In one embodiment, the body is an inner body, and the connector further comprises an outer body and an inner body and outer body sealing mechanism configured to seal the inner body and the outer body together; and an inner body and outer body retention mechanism configured to retain the inner body and the outer body together, the inner body and outer body sealing mechanism and retention mechanism being separate mechanisms.

In one embodiment, the inner body and outer body sealing mechanism is additionally configured to retain the inner body and the outer body together.

In one embodiment, the inner body and outer body sealing mechanism comprises a protrusion. Optionally, the sealing mechanism is an annular sealing protrusion.

In one embodiment, the inner body and outer body sealing mechanism comprises a complementary recess.

In one embodiment, the inner body comprises the protrusion and the outer body comprises the recess.

In one embodiment, the annular sealing protrusion comprises an angled cross-sectional profile.

In one embodiment, the annular sealing protrusion is provided on an external surface of the inner body and is configured to be in interference fit with an inner surface of the outer body.

In one embodiment, the inner body and outer body retention mechanism comprises a protrusion, preferably a barb.

In one embodiment, the inner body and outer body retention mechanism comprises a complementary indentation or aperture.

In one embodiment, the complementary indentation or aperture is defined by one or more walls, and the or each barb is positioned in the complementary indentation or aperture without abutting the one or more walls.

In one embodiment, the inner body and outer body retention mechanism protrusion is an annular protrusion.

In one embodiment, the complementary indentation or aperture is an annular indentation or aperture.

In one embodiment, the annular sealing protrusion and annular retention protrusion have different diameters.

In one embodiment, the annular sealing protrusion and annular retention protrusion have different cross-sectional profiles.

In one embodiment, the annular retention protrusion has a rounded cross-sectional profile.

In one embodiment, the annular retention protrusion has an angled cross-sectional profile.

In one embodiment, the inner body and outer body sealing mechanism comprises an interference fit between a tapered wall of the inner body and a complementary tapered wall of the outer body.

In one embodiment, a terminal end of the inner body extends beyond an end of the outer body.

In one embodiment, the inner body has a tapered outer surface with the terminal end having a wider diameter than the remainder of the inner body.

In another aspect, there is provided a combination of a connector as described above together with a second connector, the second connector having an internal passage, wherein the inner body is at least partly located in the internal passage of the second connector such that the sealing mechanism substantially seals with the internal passage and the retention mechanism engages with the exterior of the second connector and the retention mechanism is engaged with the second connector.

In one embodiment, the second connector has one or more recesses and the retention mechanism is engaged with the one or more recesses.

In one embodiment, when connected, the connectors are capable of resisting a separating force of greater than or equal to about 30N.

In one embodiment, when connected, the connectors are capable of resisting a separating force of greater than or equal to about 50N.

In another aspect, there is provided a connector for a component of a medical breathing circuit, the connector comprising: a tube connection portion for engaging with a tube, the tube connection portion defining a gases pathway, the tube connection portion having a first protrusion and a second protrusion that fall within a helical path.

In one embodiment, the helical path has a first edge, a second edge, and a width between the first edge and the second edge, and the first protrusion is positioned at the first edge of the path.

In one embodiment, the second protrusion is positioned at the first edge of the path.

In one embodiment, the second protrusion is positioned at the second edge of the path.

In one embodiment, the second protrusion is positioned between the first edge of the path and the second edge of the path.

In one embodiment, the connector has an electrical contact for electrical connection with wires in the tube.

In one embodiment, the electrical contact is configured for electrical connection with the device.

In one embodiment, the connector has alignment features for guiding wires in the tube towards the electrical contact.

In one embodiment, the alignment features allow sideway guidance of wires to the electrical contact when tube is threaded onto the collar.

In one embodiment, connector has a guide that guides the wires to the alignment features.

In one embodiment, the connector further comprises an intermediate shell that surrounds and seals the electrical contact. Optionally, the intermediate shell comprises an overmold.

In one embodiment, the material of the outer body is the same as, or is, compatible with the material of the intermediate shell.

In one embodiment, the connector has raised wall for the intermediate shell to seal the pin insert and wires.

In one embodiment, the connector has retention means for retaining the electrical contact to the alignment features.

In one embodiment, the connector has an electrical contact compartment with inner walls that taper outwardly.

In one embodiment, the electrical contact comprises an electrical contact assembly comprising an overmold provided over the electrical contact.

In one embodiment, wherein the electrical contact assembly comprises an alignment feature that comprises a protrusion configured to engage a slot on the connector.

In one embodiment, the alignment feature comprises a shoulder that engages a recess in the connector.

In accordance with another aspect, there is provided a respiratory support system comprising: a flow generator; a housing having a screen and an outlet arranged on a top surface of the housing; a tube with a connector for releasably connecting the tube with the outlet; the connector comprising: a body and a tube connection portion for engaging with a tube, the body and the tube connection portion defining a gases pathway, wherein the tube connection portion extends at an angle of more than about 0° and less than about 90° from a longitudinal axis of the body.

In one embodiment, the angle is more than about 5° and less than about 60°.

In one embodiment, the angle is more than about 10° and less than about 40°.

In one embodiment, the angle is more than about 15° and less than about 20°.

In one embodiment, the connector has an electrical contact for electrical connection with wires in the tube, and wherein the tube connection portion extends at an angle of more than about 0° and less than about 90° from a longitudinal axis of the electrical contact.

In one embodiment, the tube connection portion is axially aligned with an end of the tube.

In accordance with another aspect, there is provided a combination of a tube with a connector as described above.

In one embodiment, the material of the outer body is the same as, or is, compatible with the material of the tube.

In accordance with another aspect, there is provided connector for a component of a medical breathing circuit, the connector comprising: an inner body and an outer body, an inner body and outer body sealing mechanism configured to seal the inner body and the outer body together; and an inner body and outer body retention mechanism configured to retain the inner body and the outer body together, the sealing mechanism and retention mechanism being separate mechanisms.

In one embodiment, the inner body and outer body sealing mechanism is additionally configured to retain the inner body and the outer body together.

In one embodiment, the inner body and outer body sealing mechanism comprises a protrusion. Optionally, the sealing mechanism is an annular sealing protrusion. The inner body and outer body sealing mechanism may comprise a complementary recess. In one embodiment, the inner body comprises the protrusion and the outer body comprises the recess.

In one embodiment, the annular sealing protrusion comprises an angled cross-sectional profile.

In one embodiment, the annular sealing protrusion is provided on an external surface of the inner body and is configured to be in interference fit with an inner surface of the outer body.

In an alternative embodiment, the inner body comprises the recess and the outer body comprises the protrusion.

In one embodiment, the retention mechanism comprises a protrusion, preferably a barb. The retention mechanism may comprise a complementary indentation or aperture. The retention mechanism may comprise two or more barbs. The retention mechanism may comprise complementary indentations or apertures.

In one embodiment, the complementary indentation or aperture is defined by one or more walls, and the or each barb is positioned in the complementary indentation or aperture without abutting the one or more walls.

In one embodiment, the retention mechanism protrusion is an annular protrusion. The complementary indentation or aperture is an annular indentation or aperture.

In one embodiment, the annular sealing protrusion and annular retention protrusion have different diameters.

In one embodiment, the annular sealing protrusion and annular retention protrusion have different cross-sectional profiles.

In one embodiment, the annular retention protrusion has a rounded cross-sectional profile. In another embodiment, the annular retention protrusion has an angled cross-sectional profile.

In one embodiment, the inner body and outer body sealing mechanism comprises an interference fit between a tapered wall of the inner body and a complementary tapered wall of the outer body.

In one embodiment, a terminal end of the inner body extends beyond an end of the outer body.

In one embodiment, the inner body has a tapered outer surface with the terminal end having a wider external diameter than the remainder of the inner body.

BRIEF DESCRIPTION OF THE DRAWINGS

Specific embodiments and modifications thereof will become apparent to those skilled in the art from the detailed description herein having reference to the figures that follow, of which:

FIG. 6A to 6D are perspective views of a cover of the connector.

FIG. 7 is a perspective view of an inner body of the connector of FIG. 2.

FIG. 8 is a perspective view from below of the inner body of FIG. 7 along with a sealing member as described herein.

FIG. 9 is another perspective view of the inner body of FIG. 7.

FIG. 22 shows a cross-section of the inner body of a connector and a second connector as described herein. A sealing member on the inner body of the connector is also shown.

FIG. 22A shows a cross section of an alternative embodiment of the inner body of a connector and embodiment second connector as described herein. A sealing member on the inner body of the connector is also shown.

FIG. 23 shows an alternative retention mechanism.

FIG. 31C shows a front view of an alternative embodiment of an outer body of a connector as described herein. A conduit and electrical sub-assembly are also shown.

FIG. 31D shows a side view of an alternative embodiment of an outer body of a connector as described herein. A conduit and electrical sub-assembly are also shown FIG. 31E shows a perspective view of an alternative embodiment of an outer body of a connector as described herein. A conduit and electrical sub-assembly are also shown

DETAILED DESCRIPTION

Figure 1A:
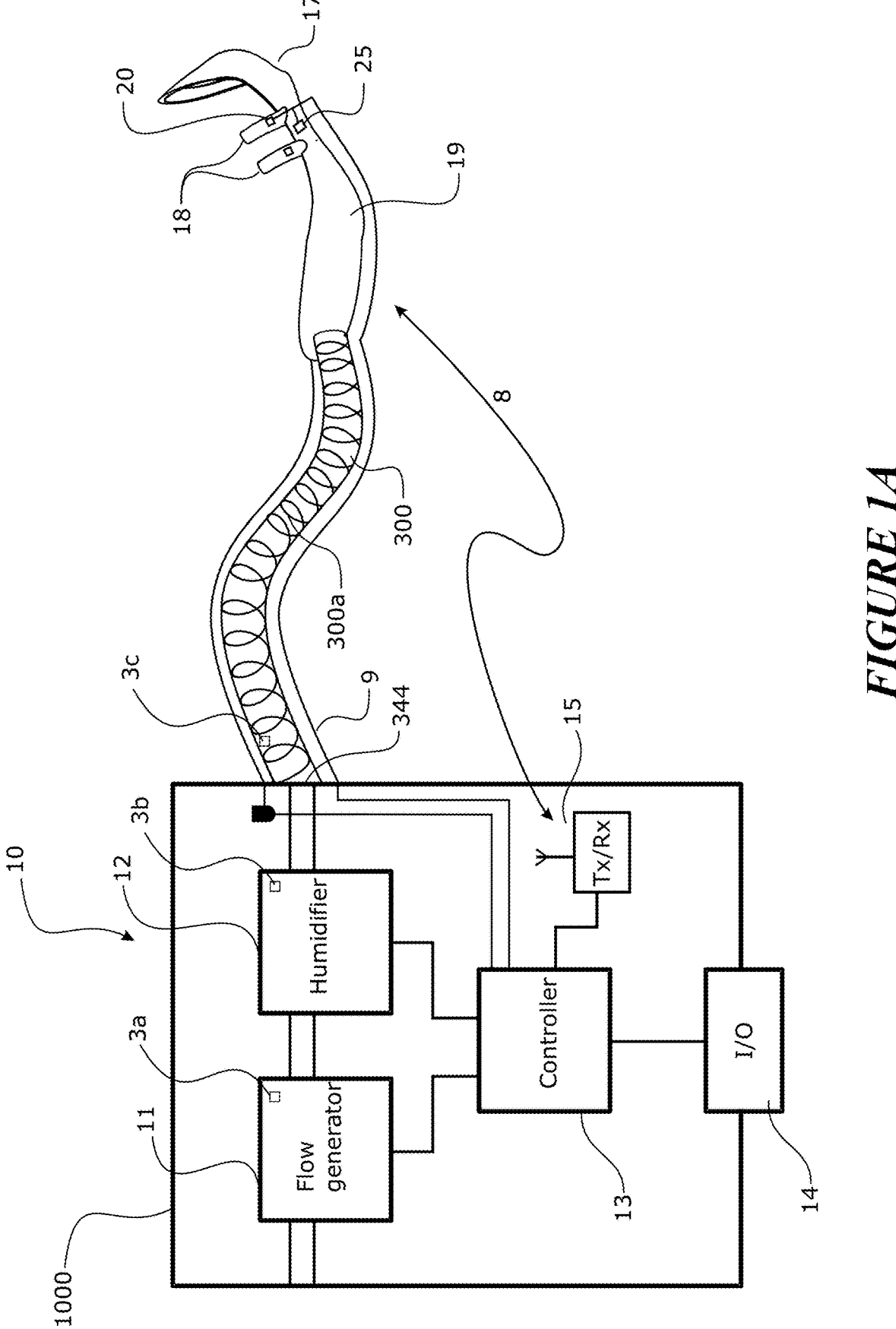
FIG. 1A shows in diagrammatic form a breathing assistance apparatus in the form of a flow therapy apparatus.
Figure 1B:
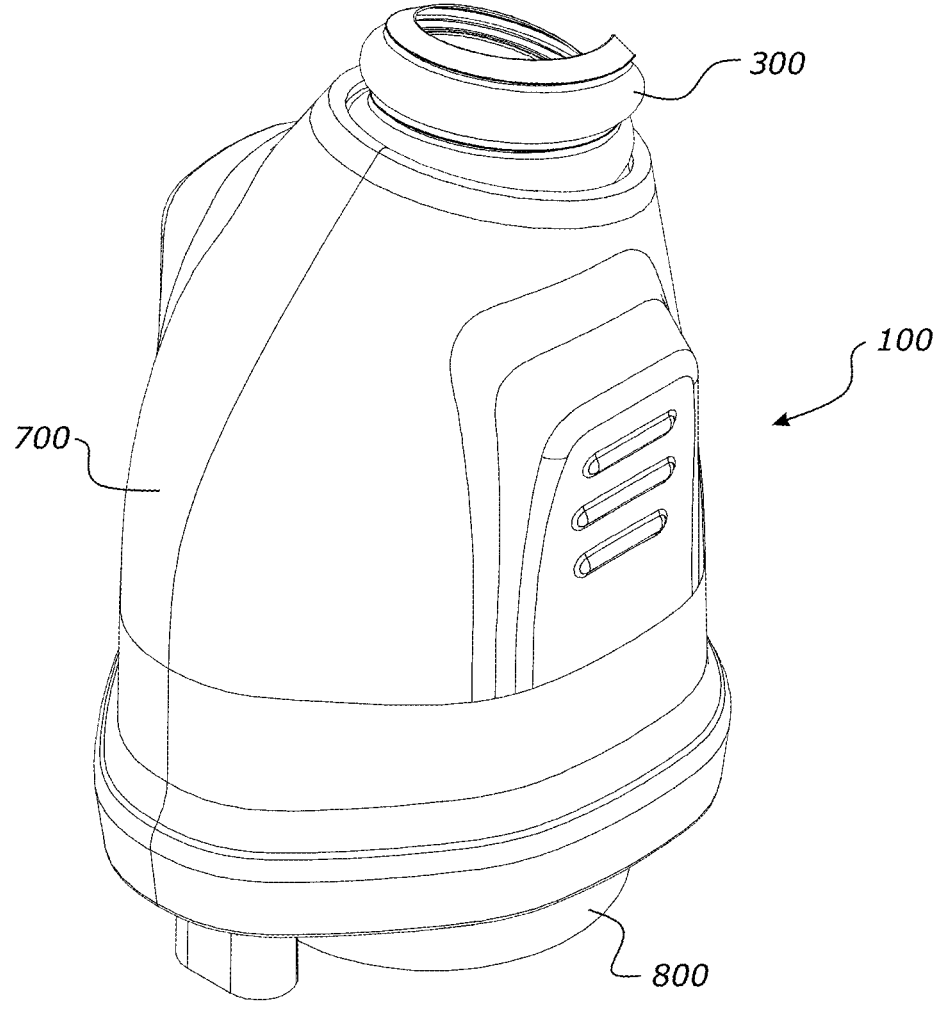
FIG. 1B is a perspective view of a connector, including a cover.
Figure 2:
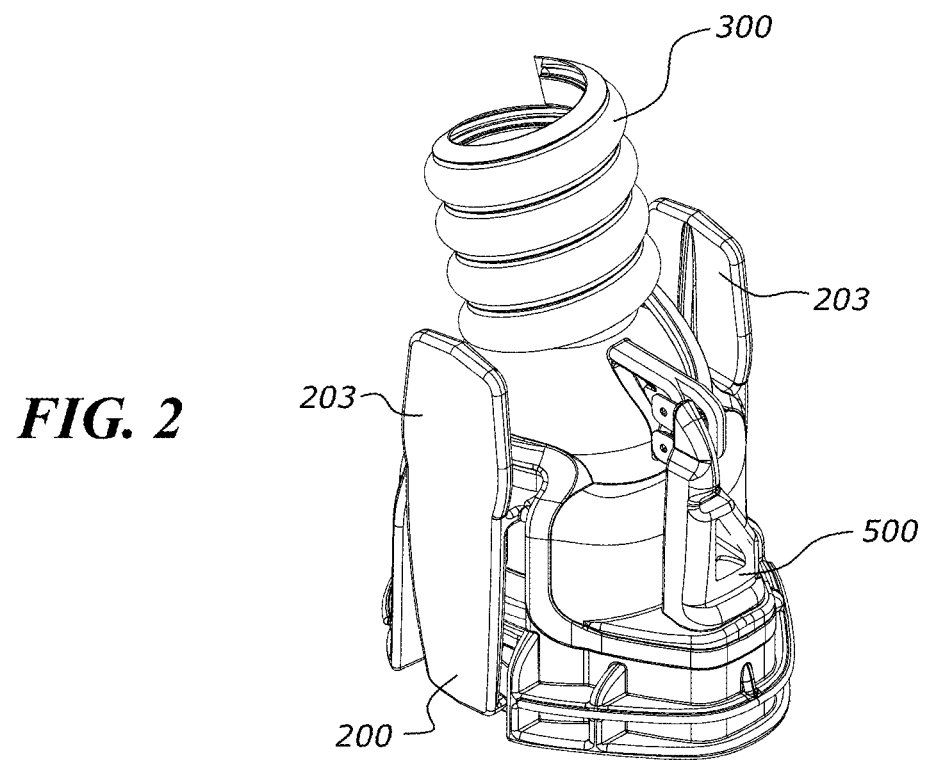
FIG. 2 is a perspective view showing components of the connector of FIG. 1, with the cover and intermediate shell removed.
Figure 3:
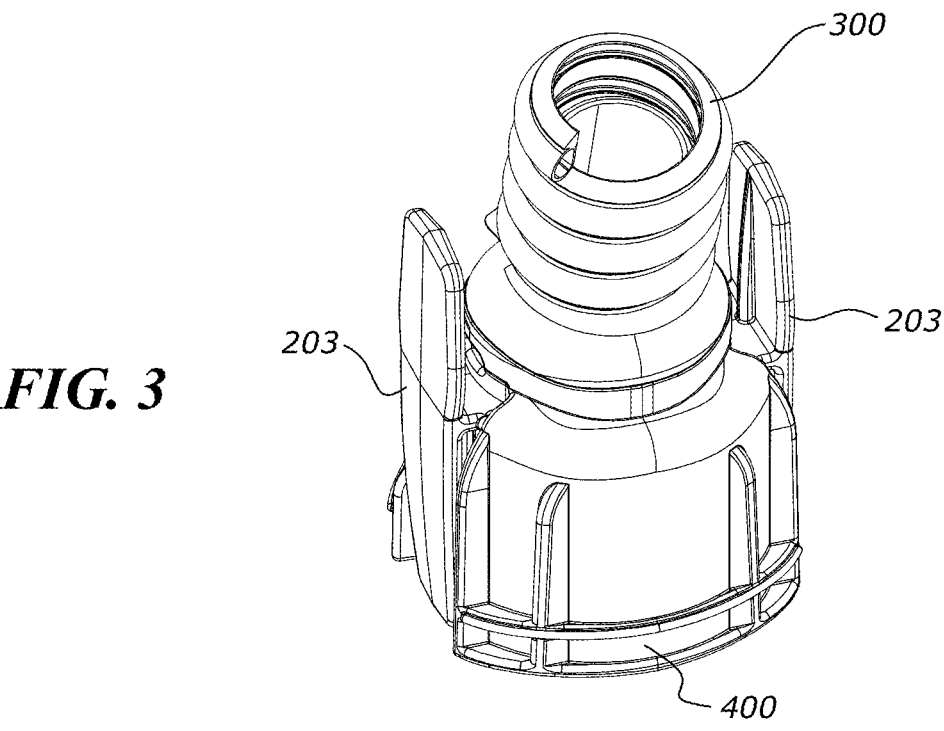
FIG. 3 is another perspective view of the components of the connector of FIG. 2.

A flow therapy apparatus 10 is shown in FIG. 1. In general terms, the apparatus 10 comprises a main housing 1000 that contains a flow generator 11 in the form of a motor/impeller arrangement, an optional humidifier 12, a controller 13, and a user I/O interface 14 (comprising, for example, a display and input device(s) such as button(s), a touch screen, or the like). The controller 13 is configured or programmed to control the components of the apparatus, including: operating the flow generator 11 to create a flow of gas (gasflow) for delivery to a patient, operating the humidifier 12 (if present) to humidify and/or heat the generated gasflow, receive user input from the user I/O interface 14 for reconfiguration and/or user-defined operation of the apparatus 10, and output information (for example on the display) to the user. The user could be a patient, healthcare professional, or anyone else interested in using the apparatus.

A patient breathing conduit 300 is coupled to a gasflow output 344 in the housing 1000 of the flow therapy apparatus 10, and is coupled to a patient interface 17 such as a nasal cannula with a manifold 19 and nasal prongs 18. Additionally, or alternatively, the patient breathing conduit 16 could be coupled to a face mask. Additionally or alternatively, the patient breathing conduit could be coupled to a nasal pillows mask, and/or a nasal mask, and/or a tracheostomy interface, or any other suitable type of patient interface. The gasflow, which may be humidified, that is generated by the flow therapy apparatus 10 is delivered to the patient via the patient breathing conduit 16 through the cannula 17. The patient breathing conduit 16 can have a heater wire 16a to heat gasflow passing through to the patient. The heater wire 16a is under the control of the controller 13. The patient breathing conduit 16 and/or patient interface 17 can be considered part of the flow therapy apparatus 10, or alternatively peripheral to it. The flow therapy apparatus 10, breathing conduit 16, and patient interface 17 together form a flow therapy system.

General operation of a flow therapy breathing apparatus 10 will be known to those skilled in the art, and need not be described in detail here. However, in general terms the controller 13 controls the flow generator 11 to generate a gasflow of the desired flow rate, controls one or more valves to control the mix of air and oxygen or other alternative gas, and controls the humidifier 12 if present to humidify the gasflow and/or heat the gasflow to an appropriate level. The gasflow is directed out through the patient breathing conduit 16 and cannula 17 to the patient. The controller 13 can also control a heating element in the humidifier 12 and/or the heating element 16a in the patient breathing conduit 16 to heat the gas to a desired temperature that achieves a desired level of therapy and/or comfort for the patient. The controller 13 can be programmed with or can determine a suitable target temperature of the gasflow.

Operation sensors 3a, 3b, 3c, 20, 25 such as flow, temperature, humidity, and/or pressure sensors can be placed in various locations in the flow therapy apparatus 10 and/or the patient breathing conduit 16 and/or cannula 17. Output from the sensors can be received by the controller 13, to assist it to operate the flow therapy apparatus 10 in a manner that provides optimal therapy. In some configurations, providing optimal therapy includes meeting a patient's inspiratory demand. The apparatus 10 may have a transmitter and/or receiver 15 to enable the controller 13 to receive 8 signals from the sensors and/or to control the various components of the flow therapy apparatus 10, including but not limited to the flow generator 11, humidifier 12, and heater wire 16a, or accessories or peripherals associated with the flow therapy apparatus 10. Additionally, or alternatively, the transmitter and/or receiver 15 may deliver data to a remote server or enable remote control of the apparatus 10.

The flow therapy apparatus 10 may comprise a high flow therapy apparatus. As used herein, "high flow" therapy refers to administration of gas to the airways of a patient at a relatively high flow rate that meets or exceeds the peak inspiratory demand of the patient. The flow rates used to achieve "high flow" may be any of the flow rates listed below. The flow therapy apparatus 10 may be any suitable type of apparatus, but in some configurations may deliver a high gas flow or high flow therapy (of e.g. air, oxygen, other gas mixture, or some combination thereof) to a patient to assist with breathing and/or treat breathing disorders. In some configurations, the gas is or comprises oxygen. In some configurations, the gas comprises a blend of oxygen and ambient air. 'High flow therapy' as used in this disclosure may refer to delivery of gases to an adult patient at a flow rate of greater than or equal to about 10 liters per minute (10 LPM), or to a neonatal, infant, or child patient at a flow rate of greater than or equal to about 1 liters per minute (1 LPM). In some configurations, for an adult patient 'high flow therapy' may refer to the delivery of gases to a patient at a flow rate of greater than or equal to about 10 litres per minute (10 LPM), such as between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. In some configurations, for a neonatal, infant, or child patient 'high flow therapy' may refer to the delivery of gases to a patient at a flow rate of between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and about 25 LPM. Therefore, a high flow therapy apparatus for use with either an adult patient or a neonatal, infant, or child patient, may deliver gases to the patient at a flow rate of between about 1 LPM and about 100 LPM, or at a flow rate in any of the sub-ranges outlined above. Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%. High flow therapy has been found effective in meeting or exceeding the patient's inspiratory demand, increasing oxygenation of the patient and/or reducing the work of breathing. Additionally, high flow therapy may generate a flushing effect in the nasopharynx such that the anatomical dead space of the upper airways is flushed by the high incoming gas flows. This creates a reservoir of fresh gas available of each and every breath, while minimising re-breathing of carbon dioxide, nitrogen, etc.

The patient interface may be a non-sealing interface to prevent barotrauma (e.g. tissue damage to the lungs or other organs of the respiratory system due to difference in pressure relative to the atmosphere). The patient interface may be a nasal cannula with a manifold and nasal prongs, and/or a face mask, and/or a nasal pillows mask, and/or a nasal mask, and/or a tracheostomy interface, or any other suitable type of patient interface.

Figure 27:
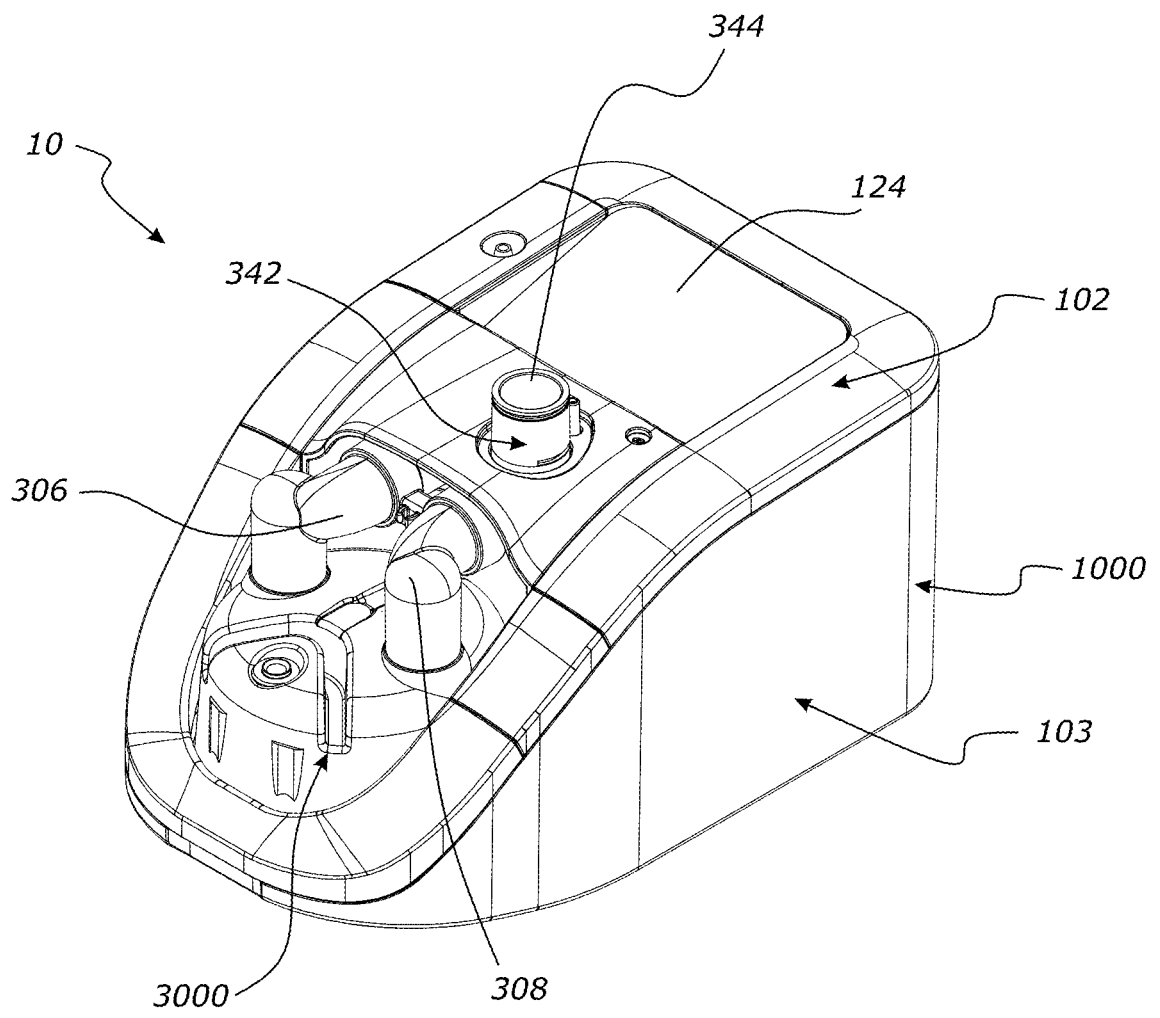
FIG. 27 shows a flow therapy apparatus.

As shown in FIG. 27, in one example embodiment, the flow therapy apparatus 10 may comprise a main housing, for example such as that shown by 1000. Such a main housing 1000 may have a main housing upper chassis 102 and a main housing lower chassis 103.

The main housing upper chassis 102 has a peripheral wall arrangement. The peripheral wall arrangement defines a humidifier or liquid chamber bay for receipt of a removable liquid chamber 3000. The removable liquid chamber 3000 contains a suitable liquid such as water for humidifying gases that will be delivered to a patient.

The removable liquid chamber 3000 comprises an outer housing defining a liquid reservoir, a liquid chamber gases inlet port 306 in fluid communication with the liquid reservoir, and a liquid chamber gases outlet port 308 in fluid communication with the liquid reservoir. A baffle may be provided internally in the liquid reservoir to define a flow path of gases through the liquid chamber 3000. A lower edge of the liquid chamber 3000 comprises an outwardly directed annular flange which interacts with guide rails in the liquid chamber bay for locating and retaining the liquid chamber 3000 in the liquid chamber bay. The flange extends outwardly from the base of a peripheral wall of the liquid chamber 3000. A bottom wall of the liquid chamber 3000 is heat conducting and is adapted for resting on the heater plate for heating liquid in the liquid chamber 3000.

The apparatus 10 comprises a connection manifold arrangement for fluid coupling of the liquid chamber 3000 to the apparatus 10. The liquid chamber 3000 can be fluidly coupled to the apparatus 10 in a linear slide-on motion in a rearward direction of the liquid chamber 3000 into the liquid chamber bay, from a position at the front of the housing 1000 in a direction toward the rear of the housing 1000. The connection manifold arrangement comprises a manifold gases outlet port that is in fluid communication, via a fixed L shaped elbow, with a gasflow passage from the motor and/or sensor module. The fixed L shaped elbow receives gases from the outlet of the blower of the motor and/or sensor module, and connects to the inlet port 306 of the liquid chamber bay 3000. The lower portion of the elbow extends downwardly into the interior of the gasflow passage tube, to receive gases from the motor and/or sensor module.

The connection manifold arrangement further comprises a humidified gases return port that is embodied in a removable elbow 342. The removable elbow 342 is L-shaped, and further comprises a patient outlet port 344 for coupling to the patient breathing conduit to deliver gases to the patient interface. The outlet port 344 is arranged towards the front of the apparatus 10 and in front of the screen 124 on the top surface of the housing 1000. The screen 124 is arranged towards the rear of the apparatus 10. The manifold gases outlet port, manifold gases inlet port, and patient outlet port 344 each comprise soft seals such as O-ring seals or T-seals (not shown) to provide a sealed gases passageway between the apparatus 10, the liquid chamber 3000, and the patient breathing conduit.

The liquid chamber gases inlet port 306 is complementary with the connection manifold gases outlet port, and the liquid chamber gases outlet port 308 is complementary with the connection manifold gases inlet port. The axes of those ports are preferably parallel to enable the liquid chamber 3000 to be inserted into the liquid chamber bay in a linear movement.

The apparatus 10 has air and oxygen (or alternative auxiliary gas) inlets in fluid communication with the motor to enable the motor to deliver air, oxygen, or a suitable mixture thereof to the liquid chamber 3000 and thereby to the patient.

General Description

With reference to FIGS. 1B to 22, a connector 100 for a component of a medical breathing circuit is shown. The connector 100 is configured to be provided at a terminal end of a conduit 300. In particular, the connector 100 forms a part of a medical breathing circuit, for a releasable, yet secure, connection between an end of the conduit 300 with another device of the circuit. The other device may be a humidifier, a flow generator, or another conduit. If the other device is a humidifier or flow generator, for example, the other device may be an outlet of the humidifier or flow generator. In the following description, the other device is referred to as a second connector 800.

The connector 100 has an inner body 200 and an outer body 400. The inner body 200 and outer body 400 define a gases pathway. In one embodiment, the connector 100 is used to connect the conduit or tube 300 to the second connector 800. When assembled, the gases pathway of the connector is in fluid communication with each of the conduit 300 and the second connector so that gas may flow from the second connector, through the connector, to the conduit 300.

The inner body 200 and the outer body 400 are separate components. The inner body 200 has a retention mechanism configured to engage the second connector, which will be described in more detail below.

The outer body 400 is configured to at least partly surround the inner body 200. When assembled together, the outer body 400 covers most of the front and the back of the inner body 200. The outer body 400 has cut outs through which part of the inner body extends. The inner body 200 also extends slightly out of the outer body 400 at its terminal end. The terminal end has a greater diameter the remainder of the inner body.

The outer body 400 has a tube engagement mechanism. The tube engagement mechanism connects the connector 100 and the tube 300 together.

The inner body 200 has a sealing mechanism configured to seal with the second connector 800. The connector also has a sealing mechanism configured to seal the inner body 200 and outer body 400. The sealing mechanism between the inner body 200 and the second connector 800 and the sealing mechanism between the inner body 200 and the outer body 400 provide a sealed pathway from the conduit 300 to the second connector 800 in which gas flow is prevented, or at least substantially inhibited, from leaking into the surrounding environment.

The connector 100 has a separate retention mechanism configured to retain the inner body 200 and the outer body 400 together.

In the embodiment shown, the inner body 200 is a unitary component that is formed as one piece. In particular, the inner body 200 comprises a first material. In some embodiments, portions of the inner body 200 may comprise the first material with other parts comprising different materials. For example, the retention mechanism of the inner body 200 comprises a flexing region. In some embodiments, the flexing region may comprise the first material and other portions of the inner body 200 may comprise a different material.

The tube engagement mechanism of the outer body 400 comprises a second material. In some embodiments, the first material is stiffer than the second material. That is, the first material has a higher elastic and/or flexural modulus than the second material. The first material may additionally or alternatively have a higher bending modulus than the second material.

The retention mechanism comprises a lever that is movable relative to the inner body 200 about the flexing region. The lever has a retention portion 203B on one side of the flexing region and an actuation portion 203A on the other side of the flexing region. The lever may be movable by being pivotable relative to the inner body. Alternatively, the lever may be movable by hinging relative to the inner body.

As shown in FIGS. 7 to 13, the retention mechanism comprises two levers. The retention mechanism (the levers) sits outside the outer body 400.

The distance between the retention portions 203B of the two levers in the disengaged configuration is equal to or less than the distance in the engaged configuration. The distance between the retention portions 203B of the two levers in the disengaged configuration is the same as the distance in the engaged configuration.

The outer body 400 has cut-outs to allow a portion of the inner body 200 to sit within the outer body 400 and a portion of the inner body 200 to sit outside the outer body.

The flexing region is provided by a bridge 205. The bridge 205 has features to align the bridge 205 with the cut-outs. As shown in FIG. 7, the features are alignment bosses 209.

In some embodiments, the retention portion 203B of the, or each, lever comprises the first material. In some embodiments, the actuation portion 203A of the, or each, lever comprises the first material. In some embodiments, the entire retention mechanism comprises the first material. In some embodiments, the entire inner body 200 comprises the first material. The first material may comprise polyoxymethylene (POM). POM is also known as acetal or acetal co-polymer. In alternative embodiments, the first material may comprise nylon, including glass-filled nylon, or acrylonitrile butadiene styrene (ABS).

In some embodiments, the second material comprises polyolefins. In some embodiments, the second material comprises polypropylene or high density polyethylene.

Inner Body

The details of the inner body 200 will now be described. As described above, the inner body 200 has a gases pathway for gas to flow between the second connector 800 and the tube 300. The gases pathway is defined by an inner wall that tapers outwardly towards the terminal end.

The inner body 200 is configured to be at least partly located in the internal passage of the second connector 800. As described above, the inner body 200 inserts within the inner passage of the second connector 800. Having a connector that inserts within the second connector 800 is advantageous for a variety of reasons, one of which is that flow path narrows in the direction of the flow. The narrowing flow path reduces the likelihood of developing dead space in stagnant areas. Stagnant areas have a variety of disadvantages, such as providing an area for nebulized medication to pool.

The inner body 200 has a conduit 201, a sealing mechanism in the form of a wiper seal 202, and a retention mechanism in the form of a lever or levers 203.

The connector 100 has a sealing and retention mechanism between the inner body 200 and the second connector 800. The outer surface of the conduit 201 is a complementary shape to the inner surface of the second connector 800 such that the two surfaces form a pneumatic seal. The pneumatic seal may be, in part facilitated by a sealing element. The sealing element may be susceptible to wear and tear over time, and may require regular replacement. The preferred embodiment is to have a seal located somewhere on the conduit 201, as this means the seal will only need to last until the conduit 300 is replaced.

In some embodiments, the sealing mechanism comprises a sealing member. One embodiment has a seal around the circumference of the conduit 201. In the embodiment shown, the sealing member is, or comprises, a wiper seal. The wiper seal may have the shape shown in the drawings. In alternative embodiments, the wiper seal could have a different cross-sectional profile, such as a t-shape or c-shaped cross-section. In other embodiments, there could be two or more wiper seals. Additionally or alternatively, the sealing member may be, or comprise, an O-ring or any other suitable seal. A wiper seal provides for easy axial movement of the two components. The inner body 200 has a recess for receiving the sealing member. The recess walls prevent, or at least substantially inhibit axially movement of the seal relative to the inner member 200. This recess can be further enhanced by a shoulder at the edge of the recess. The sealing member has an at-rest outer diameter, the at-rest outer diameter of the sealing member is larger than an inner diameter of a part which the connector connects to. That is, the at-rest outer diameter of the sealing member is larger than the internal diameter of the gas passageway of the second connector 800. The wiper seal is deflected by contact with the inner surface of the second connector 800. This provides a force between the wiper seal and the inner wall of the second connector 800 that reduces the chance of leak. Additionally, the external diameter of the wiper seal being larger than the diameter of inner wall of the second connector 800 ensures a full pneumatic seal even if the two components are slightly out of alignment, for example, if they are out of radial alignment.

Alternatively, the seal could be provided by one or more O-rings. Alternatively, any of the aforementioned sealing elements could be implemented on the inner surface of the second connector 800, however this will mean the seal is not replaced when the tube and the connector are changed. Alternatively, the seal could be provided by an interference fit between the inner body 200 and the second connector 800. An interference fit may be a taper fit. In some embodiments, the seal may be provided by an interference fit at one part of the inner body 200 and/or a sealing member such as an O-ring or wipe seal. For example, the end of the inner body 200 could be flared outwards to sealingly contact the inner wall of the second connector 800.

The seal is positioned on the inner body 200 such that the seal will sealingly engage with the second connector 800 before the electrical connectors on the device and connector engage. This results in the gases flow (which is potentially enriched with oxygen) being pneumatically sealed from the electrical connector before any electrical connection is made. Additionally, this configuration prevents a user from assembling the connector 100 with the device in such a way that the electrical connection is formed but the gases flow path is unsealed. This is particularly desirable, as oxygen rich gas being able to leak into the electrical connection could become a safety risk.

The inner body 200 can have a set of assembly guides 200B that aid in placing the seal around the inner body 200. The assembly guides 200B extend from the terminal end of the inner body 200 towards the sealing member 202. When assembling the connector 100, the seal would be stretched by a tool such that it can be slid over the base of the inner body 200. Once the seal is aligned with the recessed portion the tool would allow the seal to contract into the recessed portion. The tool, now aligned with the assembly guides, can be withdrawn, with the seal catching on the shoulder and thereby being left in the desired position.

The inner body 200 can have a spacer to correctly locate the inner body 200 within the second connector 800. The spacer can be provided in the form of one or a series of outwardly extending protrusions 215. The protrusions 215 may be in the form of vertical ribs located around the circumference of the outer surface of the inner body 200. The ribs 215 are dimensioned to substantially complement, correspond to and/or match the diameter of the inner surface of the second connector 800, so as to provide a close and/or tight fit between the inner body 200 and the second connector 800. For example, there may be a space of about 0.05 mm between the ribs 215 and the second connector.

The ribs 215 are configured to position a portion of the inner body 200 away from the passage wall of second connector 800 and to define a space between the inner body 200 and the passage wall. The ribs 215 ensure concentric alignment of the inner body 200 and the second connector 800. The ribs prevent radial movement of the inner body 200 within the second connector 800. This ensures the inner body 200 is positioned at the intended distance from the inner surface of the second connector 800, which ensures a pneumatic seal is formed between the inner body 200 and the second connector 800. The ribs extend in a direction that is generally parallel to the longitudinal axis of the inner body. In some embodiments, one or more of the ribs has an angled, tapered, radiused or otherwise profiled end 200C. Each rib has an angled or tapered end to act as an alignment guide that guides the inner body 200 within the passage of the second connector 200.

The angled or tapered surfaces 200A at the terminal end of the inner body also help position the inner body 200 within the second connector 800. They also prevent radial movement of the inner body 200 with respect to the second connector 800. These angled or tapered surfaces 200A could also help in aligning the connector with the second connector 800. The ribs 215 and/or surfaces 200A assist in ensuring optimal sealing between the inner body 200 and the second connector 800. In other embodiments, the spacer may be in the form of a single annular projection (not shown) arranged about the exterior surface of the inner body 200.

Figure 29:
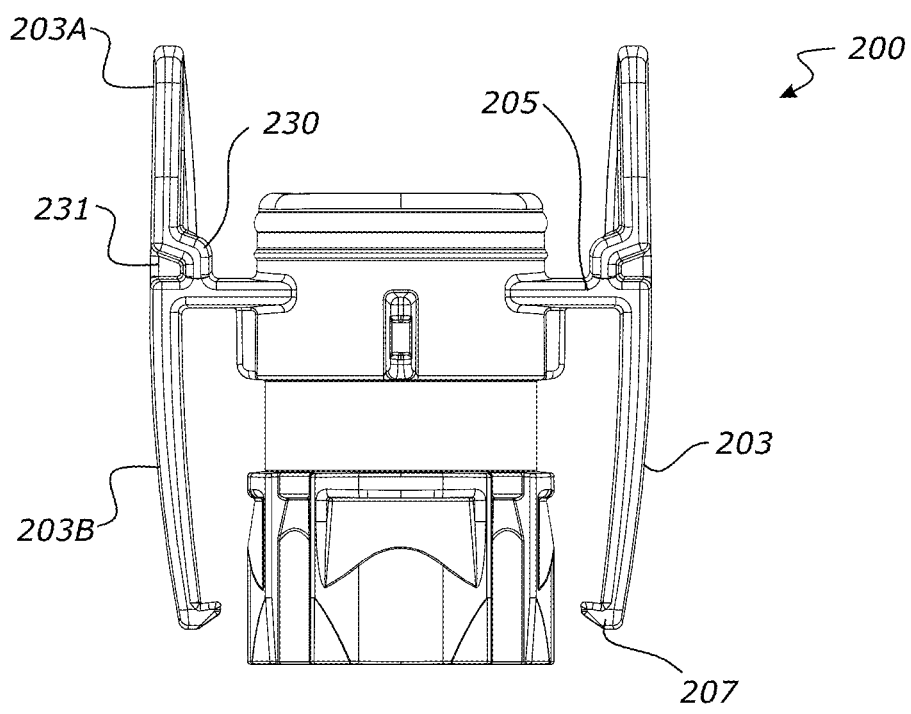
FIG. 29 shows a side view of an alternative inner body embodiment.
Figure 29A:
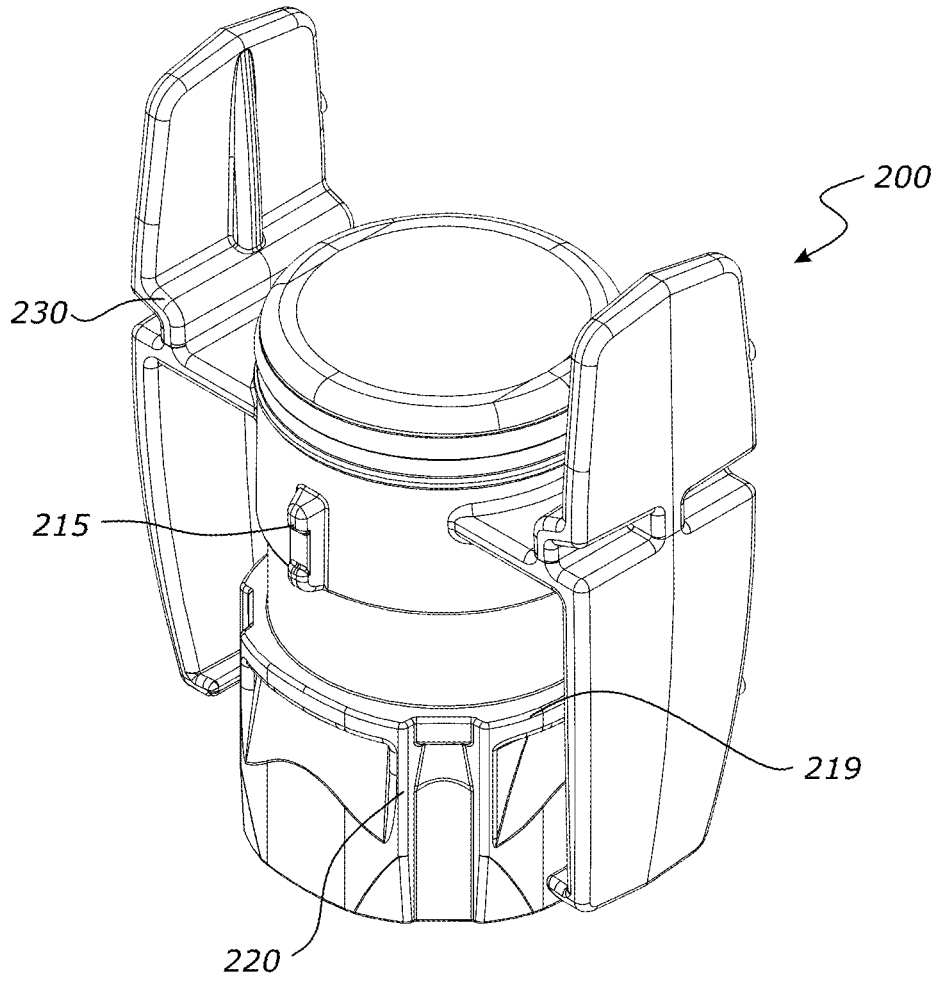
FIG. 29A shows a perspective view of an alternative inner body embodiment.
Figure 29B:
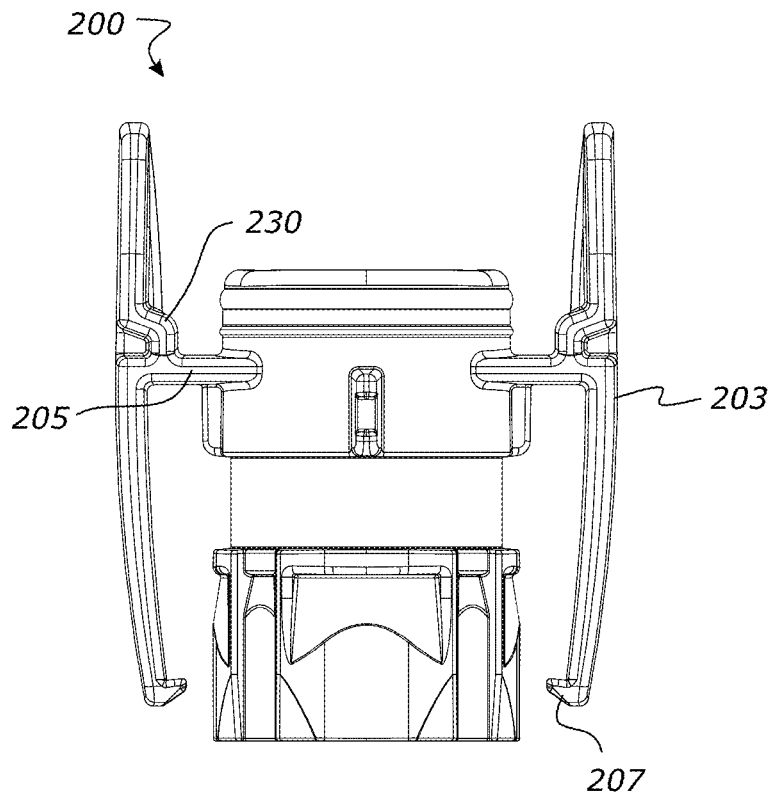
FIG. 29B shows a front view of an alternative inner body embodiment.
Figure 29C:
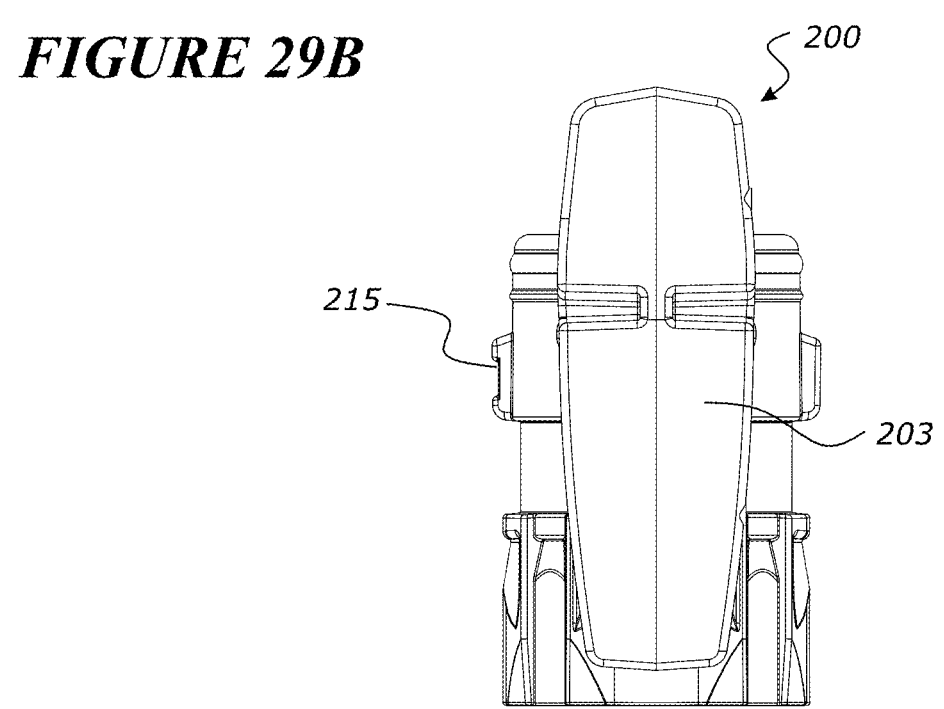
FIG. 29C shows a side view of an alternative inner body embodiment.

In an alternative embodiment as shown in FIG. 29C, one or more of the ribs 215 may be asymmetrical with other ribs—that is not all ribs may be of the same form and shapes. The ribs 215 may comprises a lead-in type feature or reduced taper or other angled radius or chamfer to assist with suitable alignment being reached.

The angled or tapered end 200C of the vertical ribs prevents, or at least substantially inhibits, the ribs from catching on the terminal end of the second connector 800 when being connected. In the embodiment shown in FIGS. 7 to 13, there are four ribs 215 that are evenly spaced around the circumference of the body thereby providing symmetry between the ribs 215 and the other features on the inner body 200. In alternative embodiments, there may be at least three ribs, for example, five, six, or seven ribs.

The sealing member is spaced at a distance from a terminal end 217. The sealing member 202 is located between the protrusions 215 and the terminal end 217 of the inner body 200. The sealing member 202 is configured to seal against the passage wall of the second connector 800 to at least substantially inhibit gas flow through the space between the inner body 200 and the passage wall. The inner body 200 has a shoulder 219 between the sealing member and the terminal end 217. A plurality of assembly ribs 220 are incorporated in this connector embodiment, extending from the terminal end 217 to the shoulder 219. These assembly ribs may advantageously aid the assembly process regarding mounting of the sealing member 202.

The inner body 200 has a wall that tapers outwardly towards the terminal end 217. The wall has an inner surface and an outer surface. The diameter of the inner wall at the terminal end 217 is greater than the diameter of the rest of the inner wall. The diameter of the outer wall at the terminal end 217 is greater than the diameter of the rest of the outer wall. The inner walls of the terminal end form a smoother/continuous profile with the inner walls of the second connector 800 end to reduce resistance to flow and dead spaces.

Located on each side of each bridge 205 is an alignment feature 209, which aids in aligning the inner body 200 with the outer body, as will be described in greater detail below. In the embodiment shown in FIGS. 7 to 13, the alignment feature 209 is a boss. In alternative embodiments, there may be more or less alignment features. For example, there may be one, two, three, five, six, or more alignment features. The alignment feature may be a hemispherical shape, or may have another suitable shape, such as a cube, cuboid, pyramid. Those shapes may have tapers to enhance the alignment properties.

Figure 4:
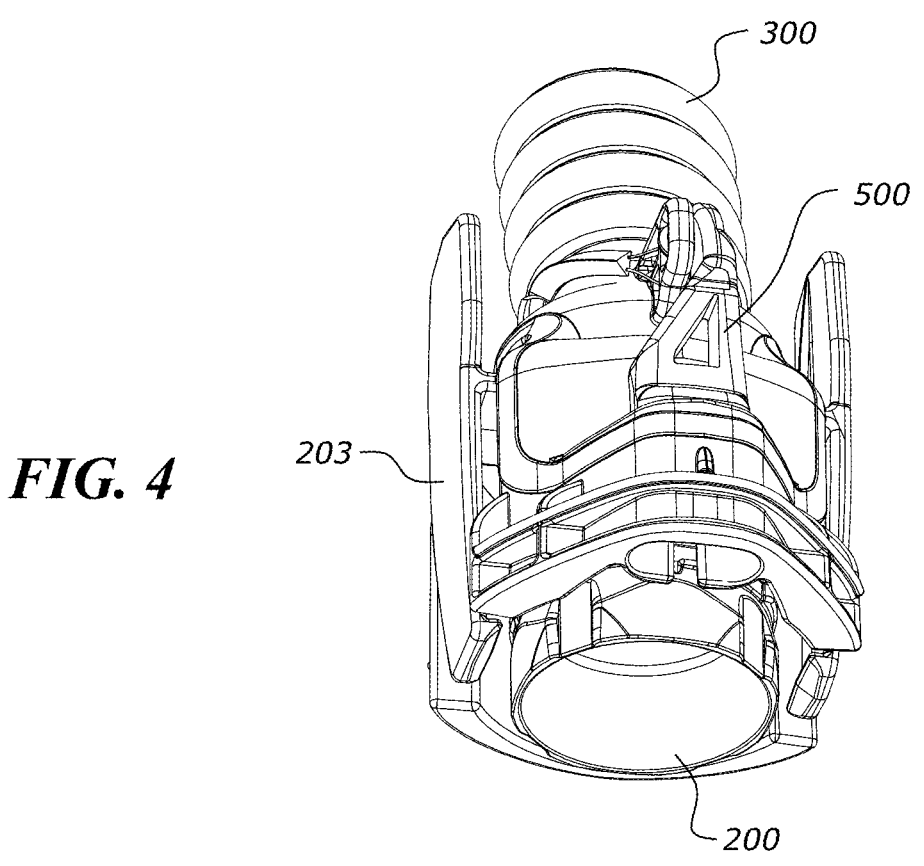
FIG. 4 is a perspective view from below of the components of the connector of FIG. 2.
Figure 5:
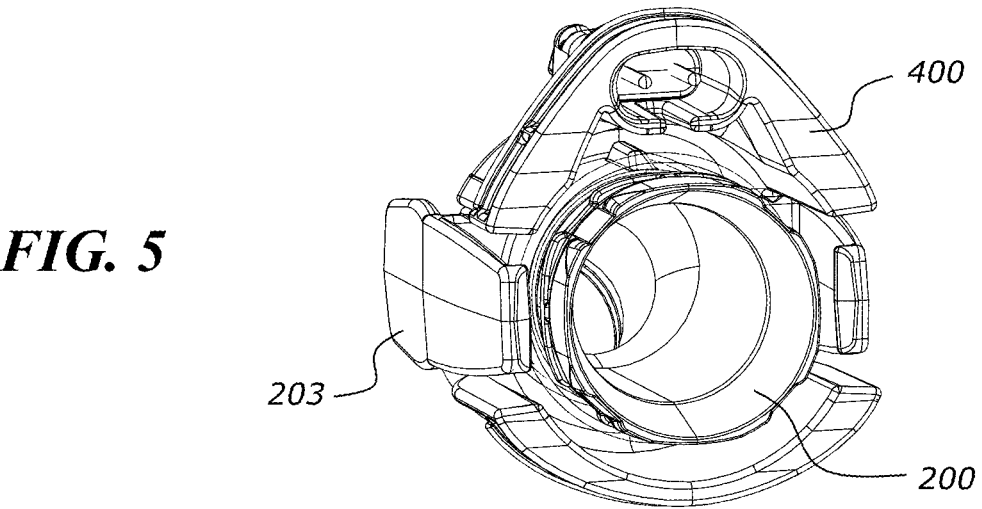
FIG. 5 is another perspective view from below of the components of the connector of FIG. 2.

As shown in FIG. 4, the terminal end of the inner body 200 extends beyond the terminal ends of the other components of the connector 400 (such as the retention mechanism, the outer body 400, and the cover 700). This would cause the terminal end 217 to engage the second connector 800 and correctly align the connector prior to other components contacting the second connector 800. The connector 100 may also include an alignment or lead in feature at the terminal end of the inner body. The alignment feature may be an inwardly tapered section of the outer wall, such that the terminal end of the inner body 200 fits into the second connecter 800 more easily, and then moves into alignment as the two components are fully connected.

The lower portion 200A of the inner body 200 has an inner surface with a diameter that approximately matches the diameter of the inner surface of the second connector 800. This creates a substantially smooth and/or continuous profile between the inner surfaces of the inner body 200 and the second connector 800 which reduces the turbulence in the gases flow path between the two components. Additionally, the potential dead space is thereby reduced, which would be undesirable, particularly when the gases flow contains nebulized medicament, as portions of nebulized medicament may condense out and/or pool in the dead space.

The inner surface of the inner body 200 then tapers from the diameter at the lower end down to a narrower diameter. The smaller internal diameter provides a profile for less turbulence. However, it also allows for space on the outer surface of the inner body 200 for various surface features, which are described in this specification.

The body is configured to be at least partly located in the internal passage of another connector, and the protrusions are configured to position a portion of the inner body 200 away from the passage wall of second connector 800 and to define a space between the inner body 200 and the passage wall, and the sealing member is configured to seal against the passage wall of the second connector 800 to at least substantially inhibit gas flow through the space between the inner body and the passage wall.

In one embodiment, the inner body is provided as a separate component that is independent of a tube or devoid of tube connection features. In one embodiment, the inner body excludes tube connection features.

Retention Mechanism

In order to retain the connector 100 when assembled with the second connector 800, the connector 100 has a retention mechanism. With reference to FIGS. 7 to 13, and 22, the retention mechanism has protrusions 207 that engage with one or more recesses of the second connector 800. These protrusions 207 are located at or near the end of a pair of levers 203, which connect to the inner member via a bridge 205. The protrusions 207 are located on a lower portion of the levers 203, while the upper portions of the levers 203 extend past the bridge 205 to form a pair of actuating tabs. Pressing inwards on the actuating tabs causes the bridge to flex and the protrusions 207 to move outwardly.

The levers 203, bridge 205 and inner member can be moulded from a material (such as acetal) that has a higher yield strength and higher elastic (Young's) and/or flexural modulus in comparison to the material of the outer body, such that the levers 203 are able to move a suitable distance without plastic deformation, yielding and/or breaking, while also providing an adequate retention force.

When no force is applied to the levers 203, the levers 203 will relax into a first, at-rest, position with a first distance between the two protrusions. When connected to the second connector 800 with the protrusions 207 engaged with the recesses 807 of the second connector 800, the levers 203 would be in a second position with a second distance between the protrusions. Preferably, the first distance would be equal to or less than the second distance. This would mean the protrusions 207 would engage with the recesses without requiring an additional force to hold them in place. Not having to force the protrusions 207 together during engagement with the connector reduces the stress on the connector during use and reduces the rate of material creep. Additionally, it may be advantageous to design the levers 203 such that in a relaxed position the protrusions 207 engage the recess but do not contact the base of the recess. This allows the levers 203 to sit in a relaxed position while engaged, further reducing the effects of creep on the material.

When the connector 100 is engaged with the second connector 800, the protrusions 207 on the levers 203 will engage with the recesses 803 in the base of the second connector 800. In the embodiment shown, the engaging faces of the recesses 803 and the protrusions 207 are substantially perpendicular to the direction of travel required to remove the conduit, such that when the protrusions 207 are engaged the connector 100 and conduit 300 cannot be pulled off the second connector 800 by even a large amount of force.

In an alternative embodiment as shown in FIG. 23, the protrusions may have a curved profile that complements the contour of the circumference of the second connector 800 or recess 803. The edges of that curved profile may be rounded to prevent damage and/or unintended engagement of a portion of recess 803 when the connector is connected to, or removed from, the outlet end.

As outlined above, the engaging faces of the recesses 803 and the protrusions may be substantially perpendicular with respect to the direction of travel. As shown in FIG. 22A, angle α illustrates an alternative embodiment. Angle α is measured with respect to the vertical centerline of inner body 200 and the angle of the protrusions 207. This angle may help prevent involuntary disconnection of the connector 100 from second connector 800 when a force along or substantially parallel to the direction of travel (being the direction indicated along the centreline of the inner body 200) is applied without a corresponding actuation/compression of the levers 203 by the user (such as inward pressing on the actuating tabs via levers 203 as described herein).

The angle α may be about 85° to about 115°, more preferably about 90° to about 110°, or preferably about 93° to about 102°, or preferably about 95° to about 99°.

In order to disconnect the connector 100 from the second connector 800, the actuating tabs are moved inwardly far enough to cause the protrusions 207 to move outwards and disengage from the recesses 807. Once the protrusions 207 are disengaged from the recesses 807, the connector can be removed with minimal resistance.

In order to connect the connector 100 to the second connector 800, the actuating tabs can be pressed inwards to move the protrusions 207 outwardly such that they can clear the outer edge of the terminal end of the second connector 800. Preferably the lower surface of the protrusions 207 can comprise an alignment or lead in feature in the form of a taper, such that when pushing the connector onto the second connector 800 the contact between the lower surface of the protrusions 207 and the terminal end of the second connector 800 pushes the protrusions 207 outwards. This could remove the need to press on the actuating tabs when connecting the connector, such that the conduit 300 can be attached to the device in a single motion.

Once the protrusions 207 have cleared the terminal end of the second connector 800, the connector can then be pushed further down until the protrusions 207 engage with the recesses. The protrusions 207 engaging with the recesses 807 could generate an audible or tactile indication that indicates to the user that the connector is engaged.

Figure 10:
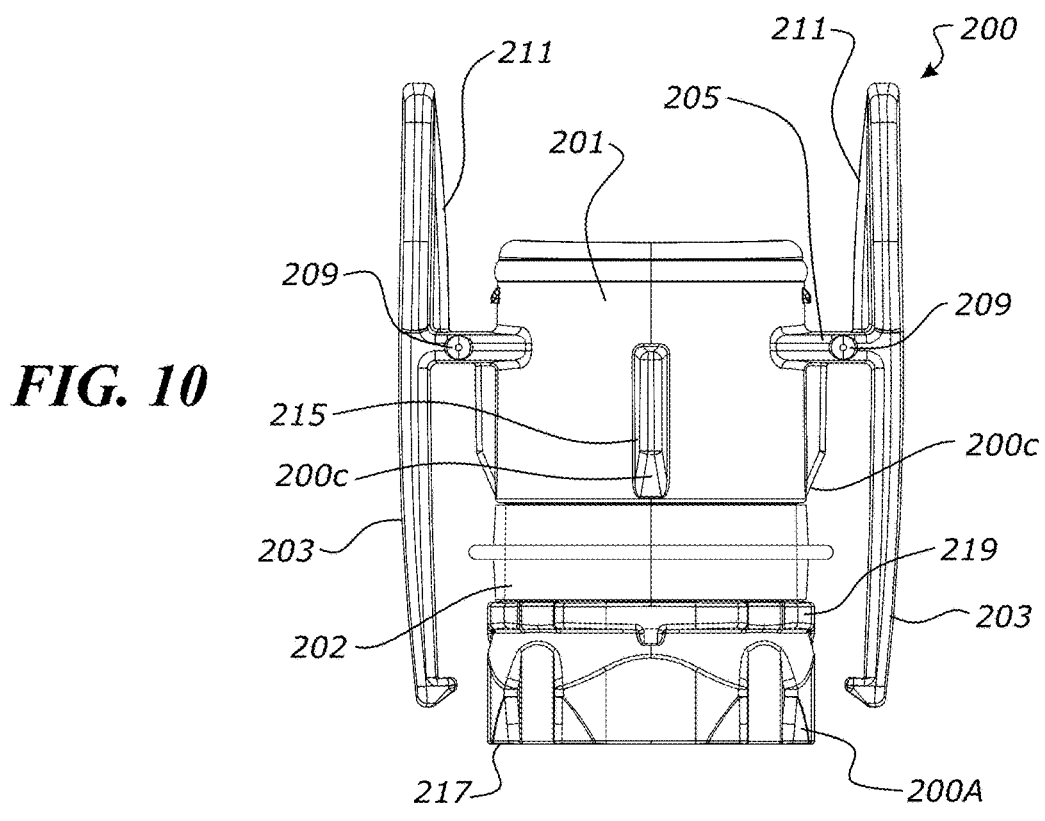
FIG. 10 is a front view of the inner body of FIG. 7.
Figure 11:
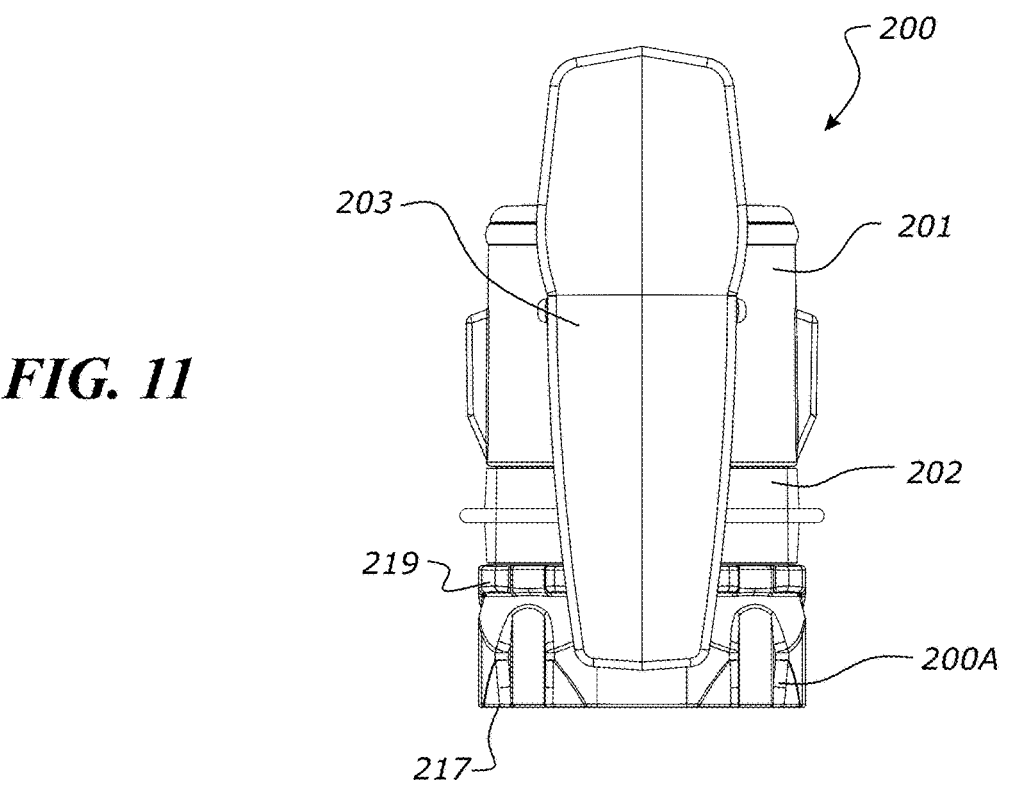
FIG. 11 is a side view of the inner body of FIG. 7.
Figure 12:
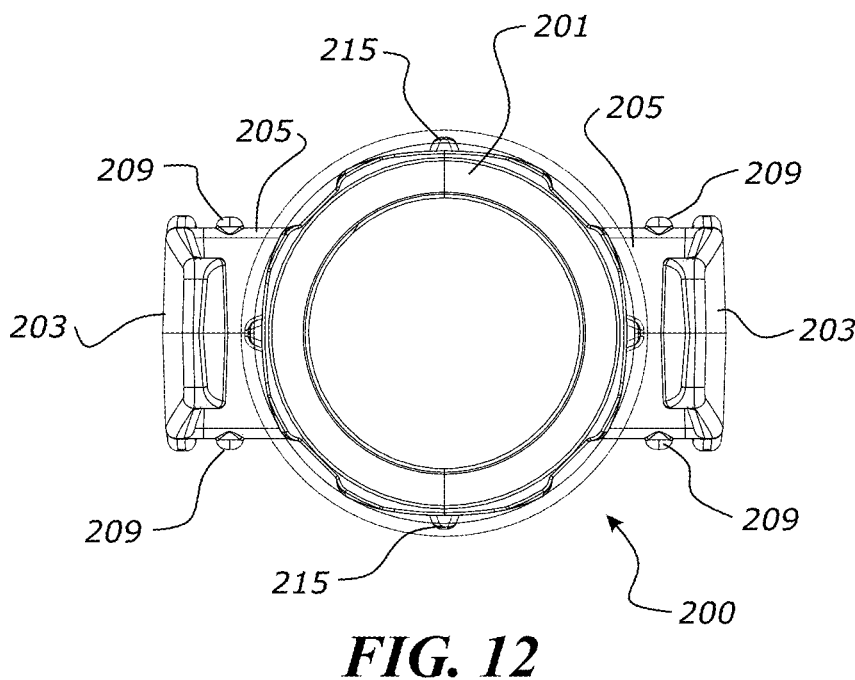
FIG. 12 is a bottom view of the inner body of FIG. 7.
Figure 13:
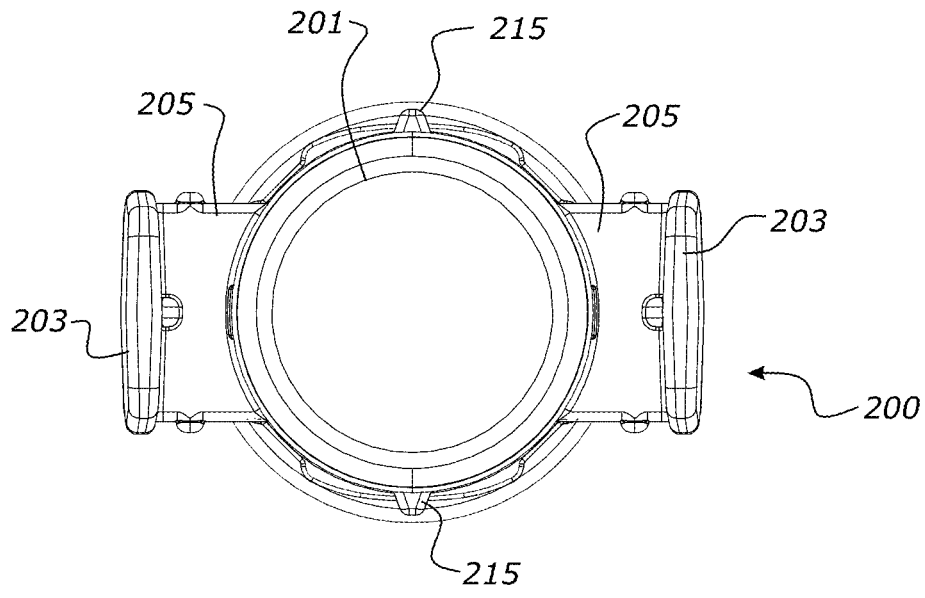
FIG. 13 is a top view of the inner body of FIG. 7.

With reference to FIG. 10, the levers 203 have a slight curve inwardly from the bridge 205 to the protrusions. The slight curve biases the protrusions 207 at the base of the levers 203 towards engagement with the recesses 807 of the second connector 800. FIG. 11 shows that the levers 203 are tapered between the bridge 205 and the protrusions, such that the width of the levers 203 at the protrusion end is less than the width of the levers 203 at the bridge 205 end. The thickness of the lever also changes along its length, for example it is thicker nearer the bridge compared to the retention end. This taper causes the terminal end of the finger to bend more easily than the flexing portion. The taper allows the portion below the bridge to bend with a more even stress distribution.

The inner surface of the actuating tabs can have one or more support ribs. The ribs increase the rigidity of the tabs such that the tabs themselves are prevented from flexing when pressed upon. If the tabs were to flex, then a large force could be placed upon the actuating tabs without producing a corresponding movement in the protrusions. By rigidizing the tabs, any movement in the tabs will be translated through the finger to the lower portion of the finger and protrusions. The tabs also have an additional function of limiting the movement of the tab itself by contacting the outer body 400 and/or the intermediate shell 600. That is, the wall of the outer body 400 acts as a stop. The amount of movement would be limited to the amount of movement that is required to actuate the protrusions, and thereby prevent excessive bending that may damage the component.

Outer Bod

With reference to FIGS. 14 to 20, the outer body 400 partially surrounds the inner body 200. The relative positions and orientations of the inner body 200 and the outer body 400 are shown in FIGS. 2 to 5. The outer body 400 and inner body 200 can be formed from a single piece, however manufacturing two components separately and then assembling them together allows for separate materials to be used (e.g. acetal for the inner body 200, polypropylene for the outer body). This would be beneficial, as certain materials with mechanical properties that would be desirable for the inner member may not be suitable for overmoulding processes, which will be described in greater detail below.

The outer body 400 serves a variety of purposes, some of which will be described in greater detail below. These can include:

Providing a connection feature that allows the conduit 300 to be attached to the connector 100.

Providing a surface on the terminal end of the connector 100 that abuts the upper surface of a device, e.g. apparatus 10 when the conduit 300 and device are connected.

Providing a receptacle for electrical pins in order to facilitate the electrical connection between the device and the conduit.

Forming a more uniform outer surface for the connector 100.

In the preferred embodiment, the inner body 200 clips into the outer body 400. As shown in the figures, an upper portion of the outer surface of the inner body 200 has an annular protrusion/flange, which preferably runs along the entire perimeter of the inner body 200. The outer body 400 comprises a corresponding recess. When assembling the connector, the inner body 200 and body are pushed together such that the protrusion on the inner body 200 clips into the recess on the outer body 400. This provides both a retention force as well as a pneumatic seal due to the tight interference fit between the protrusion and the recess.

Figure 24:
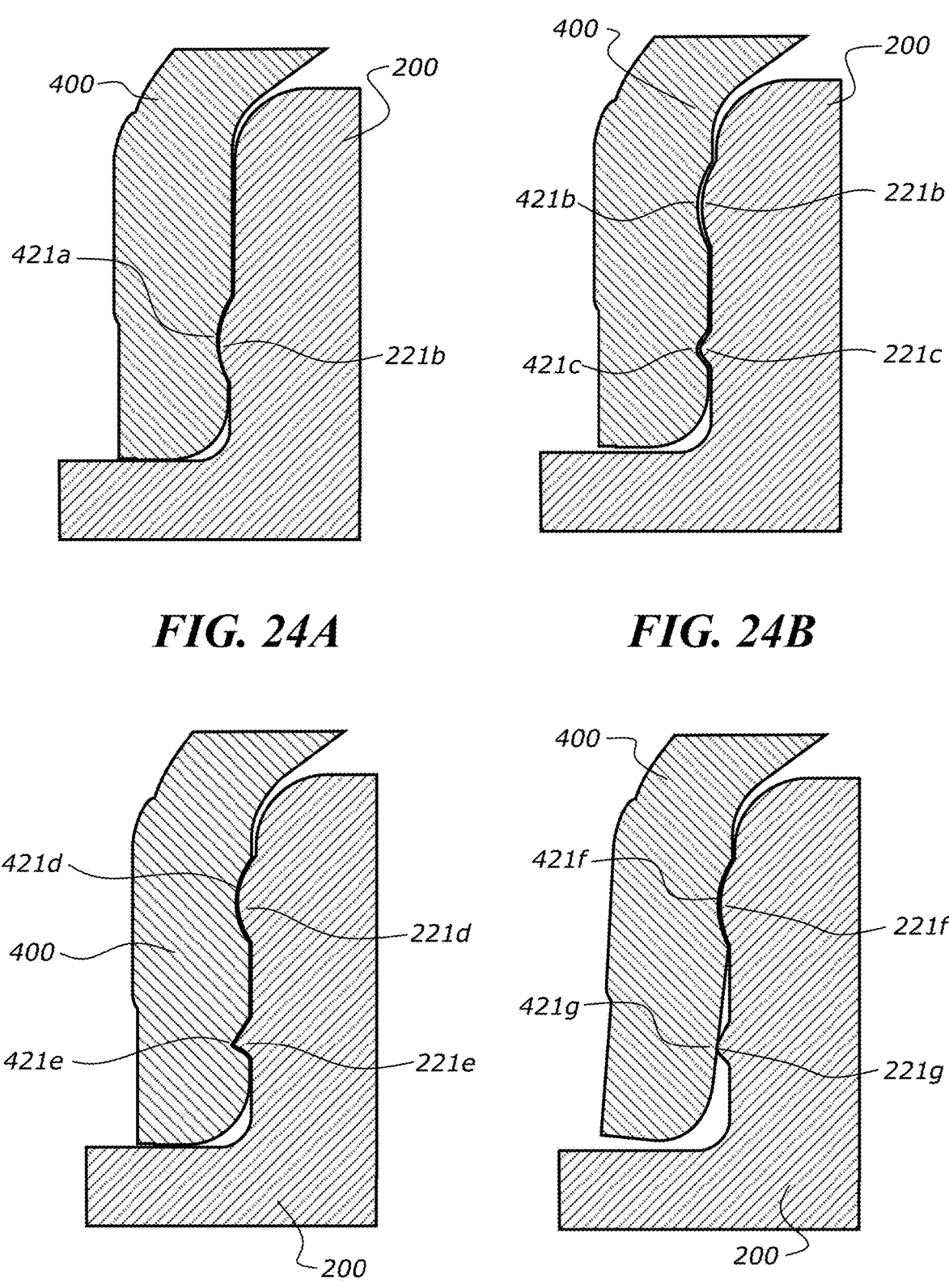
FIGS. 24A to 24D show variations of sealing and retention mechanisms between the inner body and the outer body.
Figure 25:
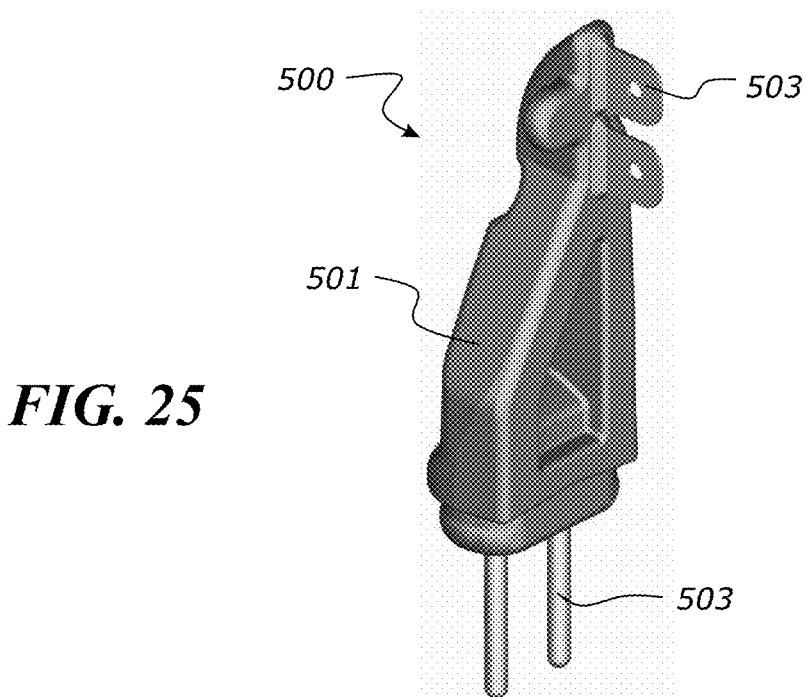
FIG. 25 shows an electrical sub-assembly.
Figure 26:
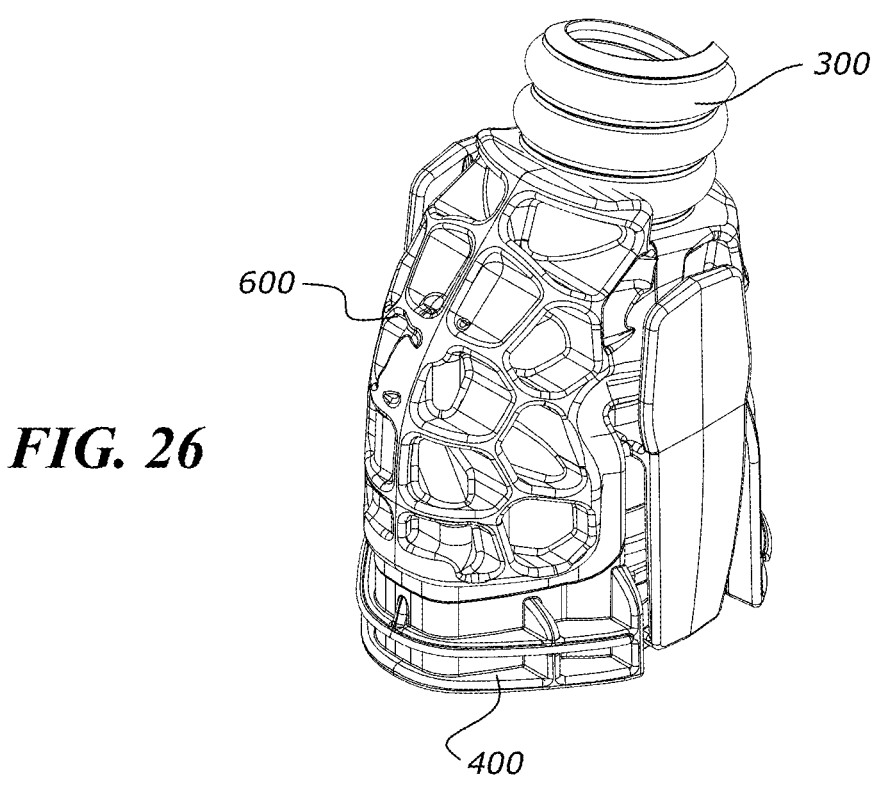
FIG. 26 is a perspective view showing components of the connector of FIG. 1B, with the cover removed.

FIGS. 24A to 24B, show variations of sealing and retention mechanisms between the inner body 200 and the outer body 400. FIGS. 24A to 24B show the inner body 200, the outer body 400, an inner body and outer body sealing mechanism configured to seal the inner body 200 and the outer body 400 together, and an inner body and outer body retention mechanism configured to retain the inner body 200 and the outer body 400 together. The inner body and outer body sealing mechanism and the inner body and outer body retention mechanism are separate mechanisms.

The inner body and outer body retention mechanism retains the inner body 200 and the outer body 400 together in a substantially permanent arrangement. The inner body 200 and the outer body 400 are not readily separated once assembled (e.g. one-time engagement). The various inner body and outer body retention mechanisms described herein prevent, or at least substantially inhibit, the inner body 200 and the outer body 400 from being separated. Once engaged, the inner body 200 and the outer body 400 cannot be easily separated, for example, those components cannot be manually separated.

In one embodiment, the inner body and outer body sealing mechanism is additionally configured to retain the inner body 200 and the outer body 400 together. In other words, the sealing mechanism comprises a second inner body and outer body retention mechanism.

FIG. 24A shows the inner body and outer body sealing mechanism in the form of an interference fit between a tapered wall of the inner body 200 and a complementary tapered wall of the outer body 400. The inner body 200 has a tapered outer surface with the terminal end having a narrower external diameter than the remainder of the inner body.

FIG. 24A also shows the inner body and outer body retention mechanism in the form of a protrusion on the inner body and a corresponding recess in the outer body. The protrusion is a rounded protrusion. The interference fit between the tapered walls of the inner and outer bodies 200, 400 can also additionally retain the inner and outer bodies 200, 400 together.

FIG. 24B shows two protrusions and complementary recesses. The protrusions are both rounded. One protrusion is larger than the other protrusion. Either protrusion may be configured as a sealing and/or retention mechanism.

FIG. 24C shows the inner body and outer body retention mechanism comprises a protrusion in the form of a barb or sharp protrusion. The inner body and outer body retention mechanism may comprise a complementary indentation or aperture. The inner body and outer body retention mechanism may comprise two or more barbs. The inner body and outer body retention mechanism may comprise complementary indentations or apertures.

FIG. 24D shows an alternative arrangement. This embodiment illustrates an inner body 200 with an annular protrusion which has a substantially rounded cross-sectional pro-
file 221*f*, and another annular protrusion that has an angled
cross-sectional profile 221*g*. The substantially rounded
annular protrusion 221*f* may be configured as a retention
mechanism, and may fit into a complementary recess 421*f* in
a corresponding outer body 400. The angled annular pro-
trusion 221*g* may be configured as a sealing mechanism
and/or may be configured to be an interference fit with a wall
of the outer body 400, for example at an interference point
421*g*.

On FIG. 24D, the inner body 200 and outer body 400
sealing mechanism comprises a protrusion 221*g*. Optionally,
the sealing mechanism is an annular sealing protrusion. The
annular sealing protrusion 221*g* comprises an angled cross-
sectional profile. The annular sealing protrusion identified as
221*g* is provided on an external surface of the inner body
200 and is configured to be in an interference fit with an
inner surface of the outer body 400, for example at a location
421*g*.

In the embodiment shown, the inner body 200 comprises
the protrusion and the outer body 400 comprises the inden-
tations or apertures. In an alternative embodiment, the inner
body 200 may comprise the indentations or apertures and the
outer body 400 may comprises the protrusion.

In some embodiments, the complementary indentation or
aperture is defined by one or more walls, and the or each
barb is positioned in the complementary indentation or
aperture without abutting the one or more walls.

Each of the variations of the inner body and outer body
retention mechanism protrusion is an annular protrusion.
The complementary indentation or aperture is an annular
indentation or aperture. In an alternative embodiment, the
indentation or aperture is an annular indentation or aperture
and the protrusion may have a shorter length, for example,
it may extend around only part of the exterior of the inner
body.

In some embodiments, the annular sealing protrusion and
annular retention protrusion have different diameters. That
is, the annular retention protrusion extends outwardly from
the inner body 200 further than the annular sealing protru-
sion.

FIGS. 24B and 24D shows the protrusions having differ-
ent cross-sectional profiles. In some embodiments, the annu-
lar retention protrusion has a rounded cross-sectional profile.
In other embodiments, the annular retention protrusion has
an angled cross-sectional profile.

The embodiments of FIGS. 24A to 24D the inner body
200 comprises the protrusion and the outer body 400 com-
prises the recess. In an alternative embodiment, the inner
body 200 may comprise the recess and the outer body 400
may comprises the protrusion.

With reference to FIGS. 24A to 24D, the connector 100
has an inner body and outer body sealing mechanism
configured to seal the inner body 200 and the outer body 400
together. The connector 100 also has an inner body and outer
body retention mechanism configured to retain the inner
body 200 and the outer body 400 together. The inner body
and outer body sealing mechanism and inner body and outer
body retention mechanism are separate mechanisms.

The inner body and outer body sealing mechanism com-
prises a sealing protrusion on the outer surface of the inner
body 200 and a complementary sealing recess in the outer
body. The inner body and outer body retention mechanism
comprises a retention protrusion on the outer surface of the
inner body 200 and a complementary retention recess in the
outer body. The terminal end 217 of the inner body 200 extends beyond an end of the outer body. The outer surface
of the terminal end 217 of the inner body 200 is tapered
outwardly.

In some embodiments, the upper end of the outer surface
of the inner body 200 may also include one or more
barbs/projections (ideally two) that correspond to cut-outs
on the outer body 400. The barbs would be located below the
annular protrusion (and therefore the cut out is located
below the annular recess) such that the barb and cut out do
not interfere with the pneumatic seal created by the recess
and protrusion.

The boundaries between the channel in the cut out and the
inner wall of body would form a sharp angle. Similarly, the
lower end of the barb would provide a flat base/surface that
is substantially perpendicular to the outer wall of the inner
body 200. When assembling the inner body 200 with the
outer body 400, the barb does not prevent the two pieces
being pushed together. The tapered portion of the barb
guides the barb into the cut-out and/or gradually pushes the
wall of the outer body 400 outwardly as the inner body 200
is received by the outer body 400. Once the barb locates
within the cut out, the interaction between the base of the
barb and the boundary of the cut out would prevent the inner
body 200 and body from being disassembled. This allows
the components to be easily assembled during manufactur-
ing, but prevents disassembly during use. That is, the
connector is configured as a 'one-time assembly' connector
so that the inner body 200 and the outer body 400 cannot be
readily disassembled or disconnected. Once assembled, the
inner body 200 and the outer body 400 are effectively
permanently connected or fixed together.

Ideally, once assembled and in a relaxed state, the barb
would not contact the walls of the cut out, e.g. the barb floats
within the cut-out. In this situation that retention force would
be provided by the interaction between the annular protru-
sion/flange and the recess.

If the barb were to contact the walls of the cut out, any
small error in the manufacturing tolerance could prevent the
annular protrusion and the recess from forming an adequate
seal. In this configuration, the barb would only contact the
base of the cut out if a large enough force is place on the
connector 100, such that the annular protrusion/flange dis-
engages from the recess. In this scenario the barb would abut
against the base of the cut out.

The force required to further disassemble the components
would be far larger than what was required to remove the
annular protrusion from the recess (specifically, the compo-
nents would likely need to be broken in order to be further
disassembled). In situations in which the protrusion has
come loose from the recess, and the barb has caught on the
cut out, the annular protrusion is shaped and configured to
re-engage the recess on its own, e.g. via forces on the
interacting surfaces of the annular protrusion and the recess.

In certain embodiments, the connector may be configured
to associate with a larger diameter tube. The tube connection
portion of the outer body would therefore have to be
configured to fit a larger diameter tube which could result in
enlarging the outer body along at least one dimension, e.g.
the diameter of the outer body could be increased. The inner
body would accordingly have to be configured to fit with a
wider (i.e. larger diameter) outer body. In certain embodi-
ments, the bridge 205 would have to be lengthened to allow
the levers 203 to sit outside the outer body. A longer bridge
205 may lead to a change in the stiffness/strength require-
ment of the bridge 205.

Figure 28:
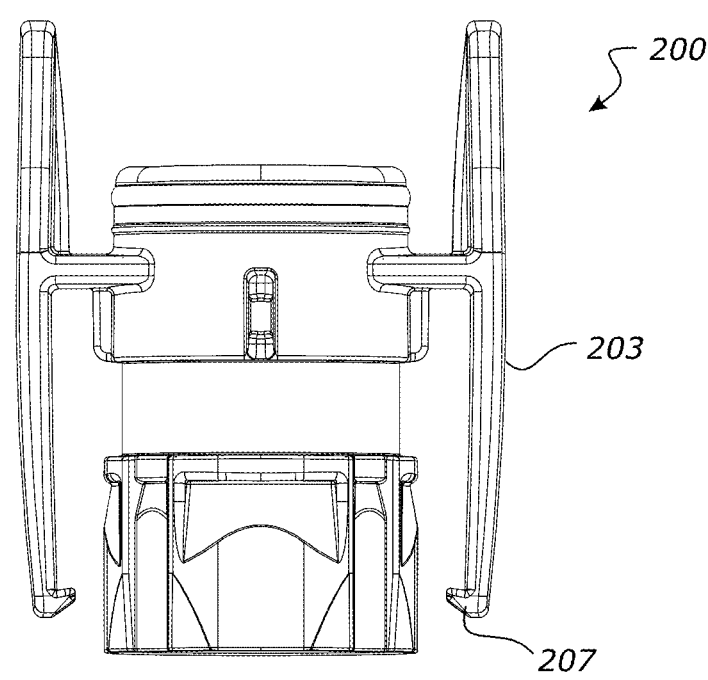
FIG. 28 shows a side view of an alternative inner body embodiment.

In the embodiment shown for example by FIG. 28, shown
is a connector 200 as an alternative configuration to that of the embodiment described with reference to FIGS. 7-13. In particular, in relation to the embodiment of FIG. 28, this configuration comprises the ribs 215, as described in relation to FIG. 29. FIG. 28 also comprises the assembly rubs 220 and shoulder 219, again as described in relation to FIG. 29.

In the embodiment shown in FIG. 29, a strengthening feature in the form of step 230 is provided to locally increases stiffness by decreasing the size of the flexing region of the bridge. The strengthening feature may also alter the hinge point of the levers 203. This allows the levers 203 with a longer bridge 205 to achieve a compressive force substantially the same as levers of a shorter bridge as described above. The strengthening feature on bridge 205 may provide flexural consistency of levers between different embodiments of the connector 100. Step 230 is provided at the intersection between the actuation portion 203A and the bridge 205.

In certain embodiments, the step 230 is provided at the intersection between the retention portion 203B and the bridge 205. In certain embodiments, the step 230 is provided on the bridge 205. In the embodiment shown, the strengthening feature on each lever 203 comprises two steps extending towards each other from opposing sides of the lever towards a central plane of the bridge.

In certain embodiments, each lever 203 may comprise a single step 230 extending from either side of the lever. In certain embodiments, the single step 230 may be provided in a substantial central position between the sides of the lever 203.

The strengthening feature may be provided to a bridge 205 of a connector regardless of its size or tube to which it connects, where the strengthening feature is used to tune the position of the hinge point along the bridge and/or compressive force required to flex the levers 203 to engage or disengage the connector 100 with the second connector 800.

In certain embodiments, the strengthening feature comprises a bridge 205 having one or more thickened portions or the entire bridge 205 may be thickened. In certain embodiments, the strengthening feature is provided at an intersection of the actuation portion 203A and the bridge. In certain embodiments, the strengthening feature is provided at an intersection of the retention portion and the bridge. In certain embodiments, the strengthening feature is provided on the bridge.

In certain embodiments, weakening feature (not shown) may be provided to the bridge to alter the position of a hinge point and/or reduce the compressive force required to flex the levers 203. The weakening feature may be in the form of a discrete thinned portion of the bridge 205 (e.g. a step in the bridge 205), a plurality of discrete thinned portions of the bridge 205 (e.g. the bridge 205 is textured, e.g. with dimples) or the entire bridge is thinned.

In certain embodiments, the weakening feature is provided at an intersection of the actuation portion 203A and the bridge. In certain embodiments, the weakening feature is provided at an intersection of the retention portion and the bridge. In certain embodiments, the weakening feature is provided on the bridge.

The strengthening and weakening features can be used to tune the flex in the levers 203 and/or the force required to move retention portion 203B towards or away from the centre of the connector 100. In certain embodiments, the bridge comprises one or more strengthening features. In certain embodiments, the bridge comprises one or more weakening features. In certain embodiments, the bridge comprises one or more strengthening features and one or more weakening features.

In the embodiment of FIG. 29 where the connector comprises a strengthening feature, a link portion 231 is provided to join the actuation portion 203A and retention portion 203B of lever 203 to ensure a movement of the actuation portion 203A towards the centre of the connector 100 translates to a movement of the retention portion 203B away from the centre of the connector 100.

Without the link portion 203, the step 203 would extend substantially across and between the sides of the lever 203, creating an additional hinge point about which the actuation portion 203A may pivot. In such an embodiment, the actuation portion 203A may require a greater actuation force and/or distance of travel before causing the retention portion 203B to move away from the centre of the connector 100. In certain embodiments, the connector comprises one or more link portions 231 and one or more steps 230. In certain embodiments, the connector comprises a plurality of link portions 231 and a plurality of steps 230.

Figure 29D:
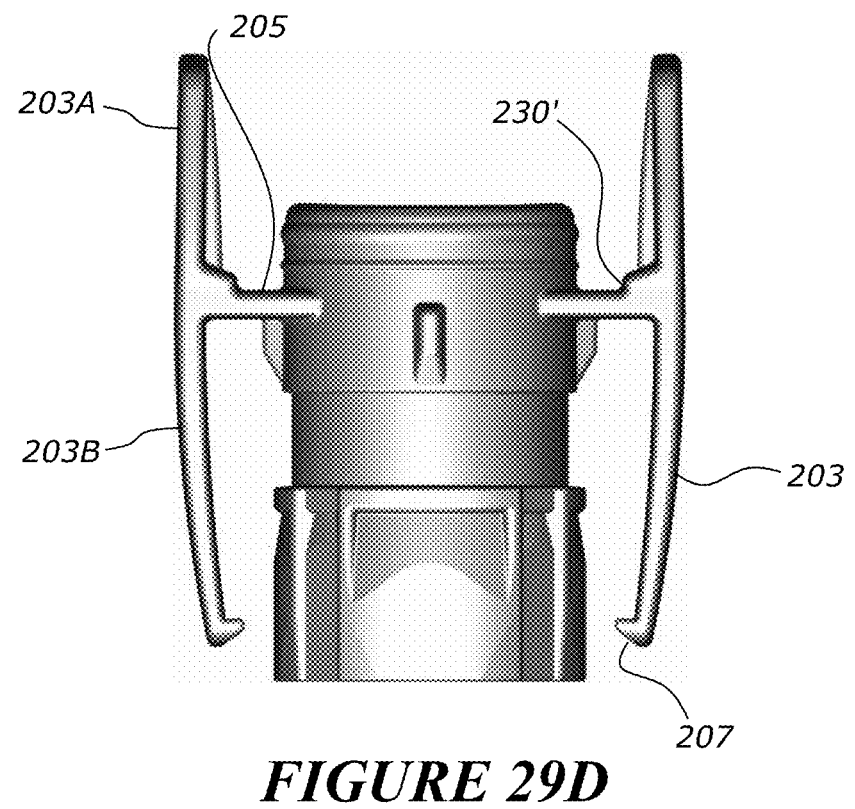
FIGS. 29D and 29F show side views of example alternative inner body embodiments.
Figure 29E:
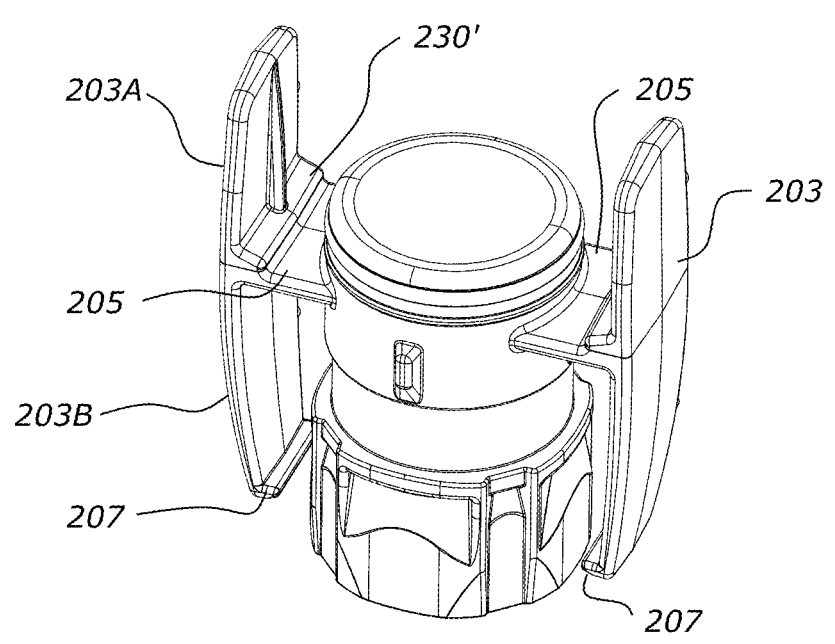
FIGS. 29E and 29G show perspective views of example alternative inner body embodiments.

FIGS. 29D and 29E illustrate various example embodiments of alternative strengthening features 230', in alternative to the step 230 outlined above. The strengthening sections 230 and 230' facilitate the translation of a force applied to the actuation portion 203A (such as radially inwardly) to help with the release of the retention mechanism protrusions 207 at the end of the retention portion 203B being relieved of its position from recess 803. Such a strengthening may further assist with resisting torsional or other deflection of the lever in the bridge region 205 (such as when a force is being applied to the levers 203 when a user is making a connection or a disconnection between the connector 100 and second connector 800.

In FIGS. 29D-29G, the strengthening features 230' are provided as intersection portions between the actuation portion 203A and bridge 205.

In FIGS. 29D-29E, a thickened strengthening feature 230' comprises a step and extends from one side of the lever 203 to the other side of the (same) lever 203, that is the strengthening feature 230' extends from one edge or side to another edge or side of the width of the bridge, or substantially across the bridge inter-connection with the lever 203. In an alternative embodiment, the strengthening feature 230' may extend at least partway between the edges or sides of the lever 203.

Figure 29F:
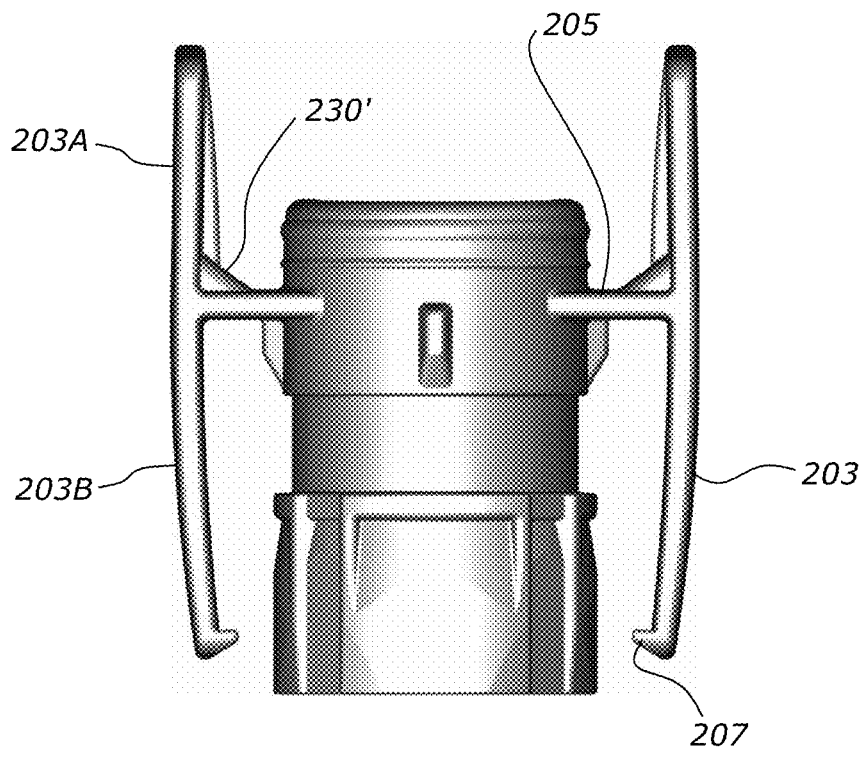
Figure 29G:
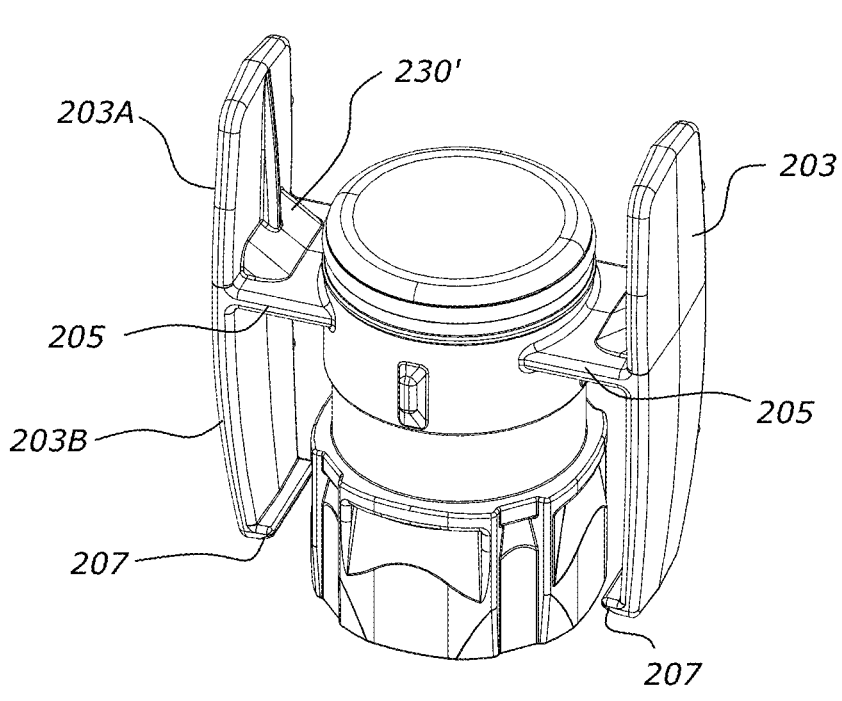

In FIG. 29F-29G, the strengthening feature 230' comprises a slope and extends at least partway between the edges or sides of the lever 203. The strengthening feature 230' (which may be a thickened intersection portion between the bridge and the lever) is positioned substantially centrally between the sides of the lever 203.

As shown from the figures, the bridge 205 is arranged between the actuation portion 203A and the retention portion 203B. As noted above, the bridge 205 may comprise a strengthening feature 230 or 230'. The strengthening feature may comprise a step (or other junction) at an intersection between the actuation portion 203A and the bridge 205.

The strengthening feature 230, 230' may comprise two (or more) steps extending towards each other from opposing sides or edges of the lever towards a central plane of the bridge 205.

The strengthening feature 230, 230' may comprise a thickened portion of the bridge 205. The thickened portion may be provided at an intersection of the actuation portion 203A and the bridge 205.

The actuation portion 203A may comprise a rib (or other reinforcement or strengthening portion) that substantially limits flexing or deflection of the actuation portion 203A when a force is applied thereon.

Tube Connection

With reference to FIGS. 14 to 19 and 21, the connector 100 has a tube connection portion 403 for engaging with the conduit 300. In the embodiment shown, the tube connection portion 403 is a portion of the outer body 400. In other embodiments, the tube connection portion 403 is a portion of the inner body 200. The tube connection portion tube connection portion 403 defining a gases pathway. The gases pathway is in fluid communication with the gases pathway of the inner body.

With reference to FIGS. 14 to 19 and 21, the outer body is provided with the tube connection features and the inner body is devoid of tube connection features. The outer body comprises the tube connection features, such that, when an assembly of the inner body and the outer body is made said assembly is connected to the tube via tube connection features of the outer body only.

The tube connection portion 403 is a tubular member. The tube connection portion 403 has at least a pair of protrusions 407 that fall within pathway. The pathway has a generally helical profile such that the conduit 300, which has an internally threaded surface, may be threaded onto the tube connection portion 403.

In some embodiments, the protrusions 407 may be axially arranged on one side of the tube connection portion 403. That is, there may be two or more protrusions 407 on one side of the tube connection portion 403. The axially aligned protrusions 407 will also fall within the helical pathway.

In alternative embodiments, the tube connection portion 403 may include an external thread. The thread may be a full thread that extends about the tubular member. Alternatively, the thread may be a partial thread having short portions of thread with gaps or spaces between the short portions.

The conduit 300 may be spirally wound, with the path of the protrusions 407 on the tube connection portion 403 being arranged to generally match the taper/helical arrangement of the spirally wound conduit. In some embodiments, the path of the protrusions does not precisely match the helical arrangement of the spirally wound conduit, but the path is designed such that the location of the protrusions will engage with the thread of the tube 300. The protrusions arranged such that they are positioned at an edge/boundary of the internal threaded portion of the tube 300. Using a series of protrusions 407 instead of a typical helical thread makes the assembly more tolerant of variances in tube diameters.

Preferably, the protrusions 407 would be arranged to match a single revolution of the taper, with only the first and last protrusion being axially aligned. The first and last protrusion 407 being axially aligned also prevents, or at least substantially inhibits, axial movement of the tube, as will be described below.

The conduit 300 may be a composite structure made of two or more distinct components that are spirally wound to form an elongate tube. A suitable conduit is the tube described in WO/2012/164407, which is incorporated herein in its entirety. The protrusions 407 would be placed to line up with this tube, such that the protrusions engage with the member by causing the hollow lumen to be compressed.

A second spirally wound member may be interwoven with the first member, with the second member being made of solid plastic. The windings of the second member on either side of the first member would prevent axial movement of the conduit 300 once the protrusions are engaged with first member, as the second member would be substantially incompressible and therefore unable to pass over the protrusion. Slight axial movement could still be possible due to the first member being slightly wider than the protrusions themselves, thereby allowing the protrusions 207 to shift between the boundaries created by the two adjacent windings of the second member.

Figure 21:
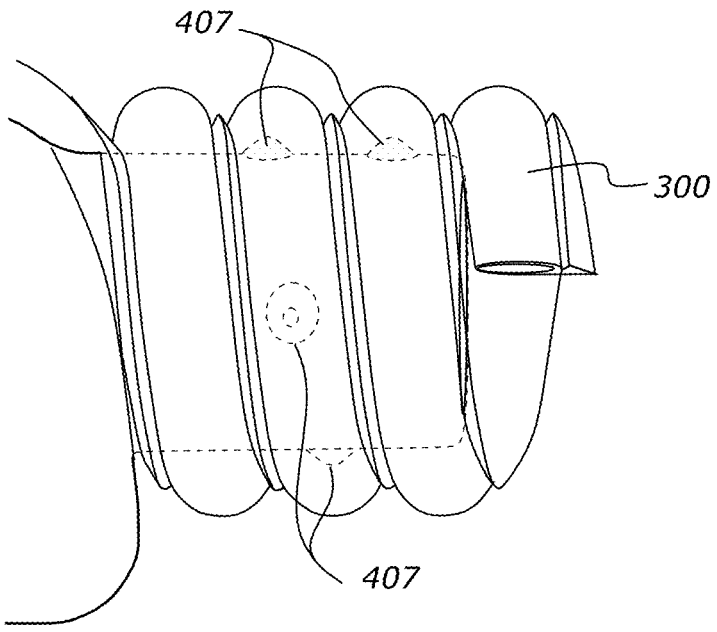
FIG. 21 is a partial view of the tube connection portion and a tube.

This axial movement may be prevented/limited by the two axially aligned protrusions 407 described above. The placement of the protrusions 407 can be altered such that one of the protrusions 407 engages with the lower boundary of the first spiral member, while the other protrusion 407 engages with an upper boundary of the first spiral member FIG. 21 shows an embodiment in which the two axially opposing protrusions provide a similar function).

In some embodiments, the location of the protrusions 407 may be chosen or designed such that the protrusions pinch adjacent/neighbouring helical portions of the tube. During manufacturing, before the conduit 300 and outer body 400 are connected, the wires of the conduit are exposed. The outer body 400 could have an alignment or lead in feature that locates the exposed wires of the breathing conduit. The alignment or lead in feature would comprise tapered channels, which taper from a wide entrance down to a narrow exit. This allows the wires to be reliably guided towards the desired location, such that the electrical contacts on the terminal end of the wires may be soldered onto the electrical pins, as is described below.

Figure 30:
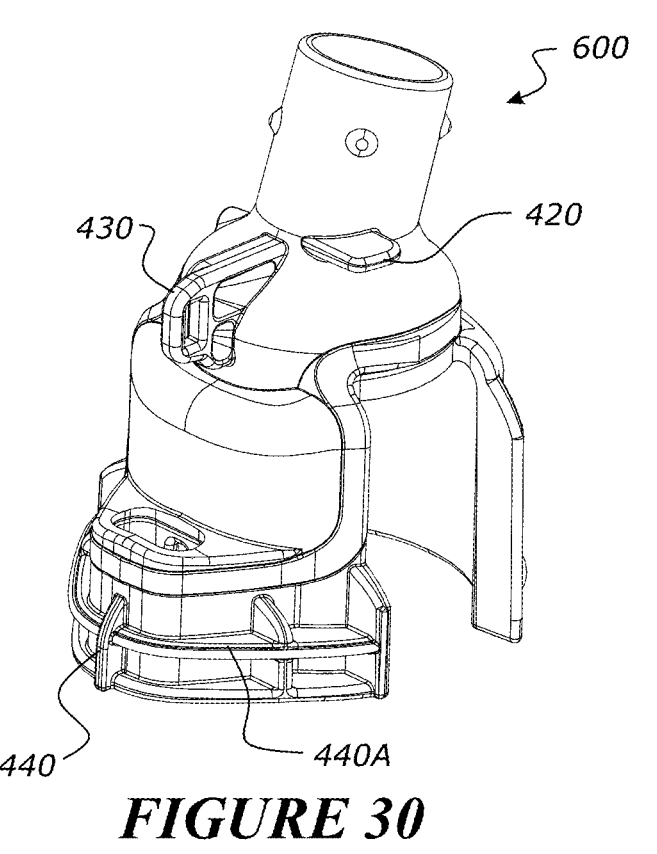
FIG. 30 shows a perspective view of an alternative embodiment of an outer body of a connector as described herein.
Figure 31:
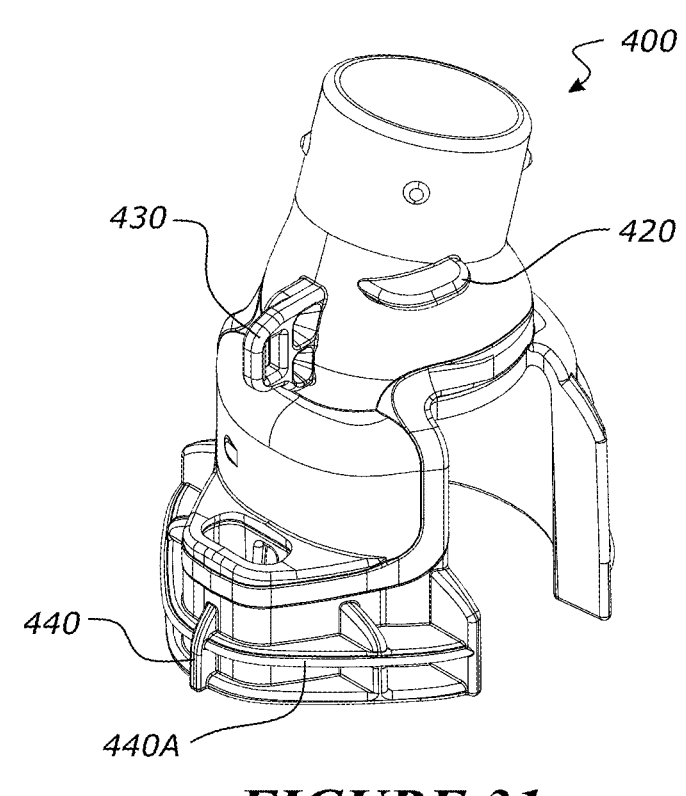
FIG. 31 shows a perspective view of an alternative embodiment of an outer body of a connector as described herein.

With reference to FIGS. 30 and 31, a projection 420 may be provided as an alignment or a lead in for a reinforcement feature of a conduit 300 as disclosed herein. The projection 420 may be provided as a radially outwardly extending projection, and provide for a guide to a conduit tube 300 as described herein.

In an example embodiment, the projection 420 may take the form of a rib or fin shaped portion 420. The projection 420 may advantageously aid in assembly of the connector and conduit, and may prevent disconnection during the over mould process as described herein.

The projection 420 may comprise a raised protrusion configured to separate a reinforcement feature of a conduit and guide the reinforcement feature (along with any other portion of a conduit which is removed when the reinforcement feature is separated) towards a wire separating protrusion 430.

The wire separating protrusion 430 may be configured to separate, or maintain separation of, or guide, two or more wires in the reinforcement feature of the conductor, for attachment to electrical pins as described below.

The tube connection portion may be placed at an angle such that the flow path of the initial section of the conduit 300 is at an angle to the flow path through the final section of the second connector 800. This would offset the initial section of the conduit 300 from a direction perpendicular with the surface of the device. The angle could direct the conduit 300 towards the front of the device, such that the conduit 300 is more likely to bend towards the front of the device, as opposed to the back of the device where it might obscure a screen 124 of the device.

A greater angle between the second connector 800 and tube connection portion is more likely to encourage the conduit to extend in a direction away from the screen 124, while a lesser angle will provide less impedance to flow of gas through the conduit 300. The angle could be between 0° (i.e. parallel to the second connector 800) and 90° (i.e. perpendicular to the second connector 800), or between or about 5° and about 45°, or between or about 10° to about 30°, or between or about 15° to about 20°, or between any two angles mentioned.

Figure 14:
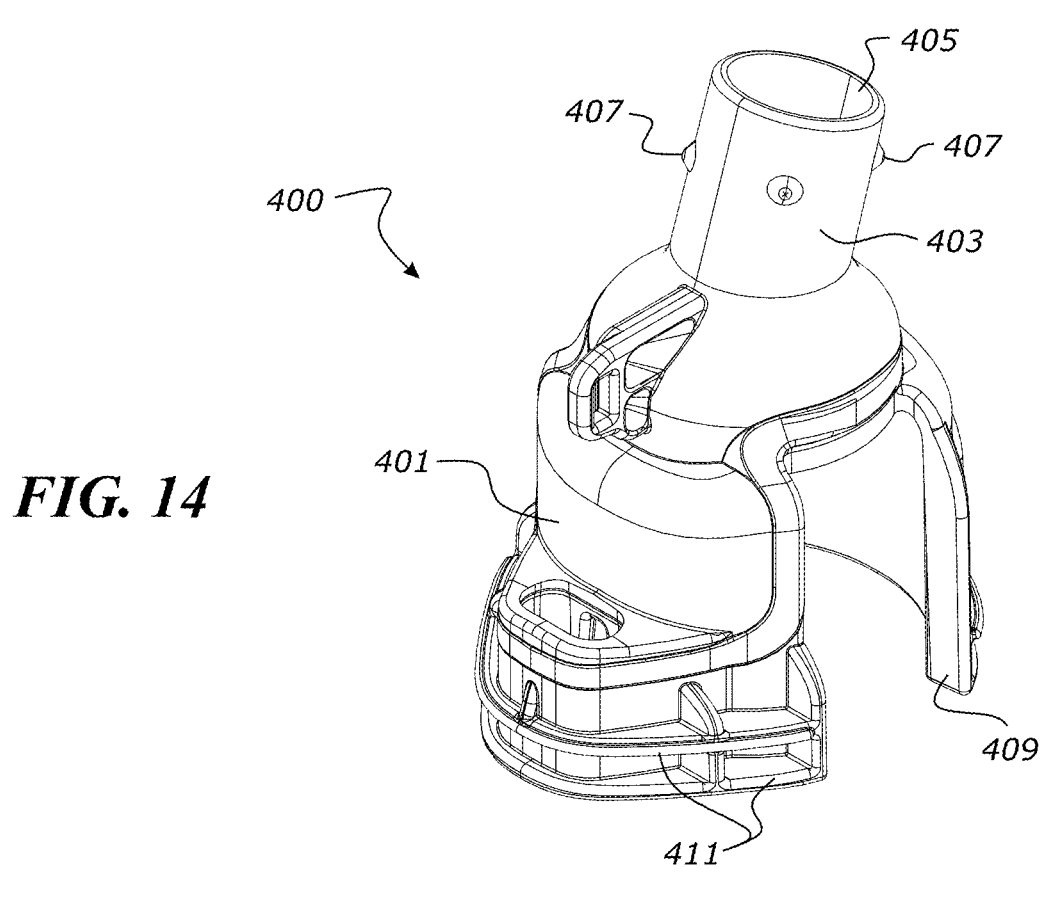
FIG. 14 is a perspective view of an outer body of the connector of FIG. 2.
Figure 15:
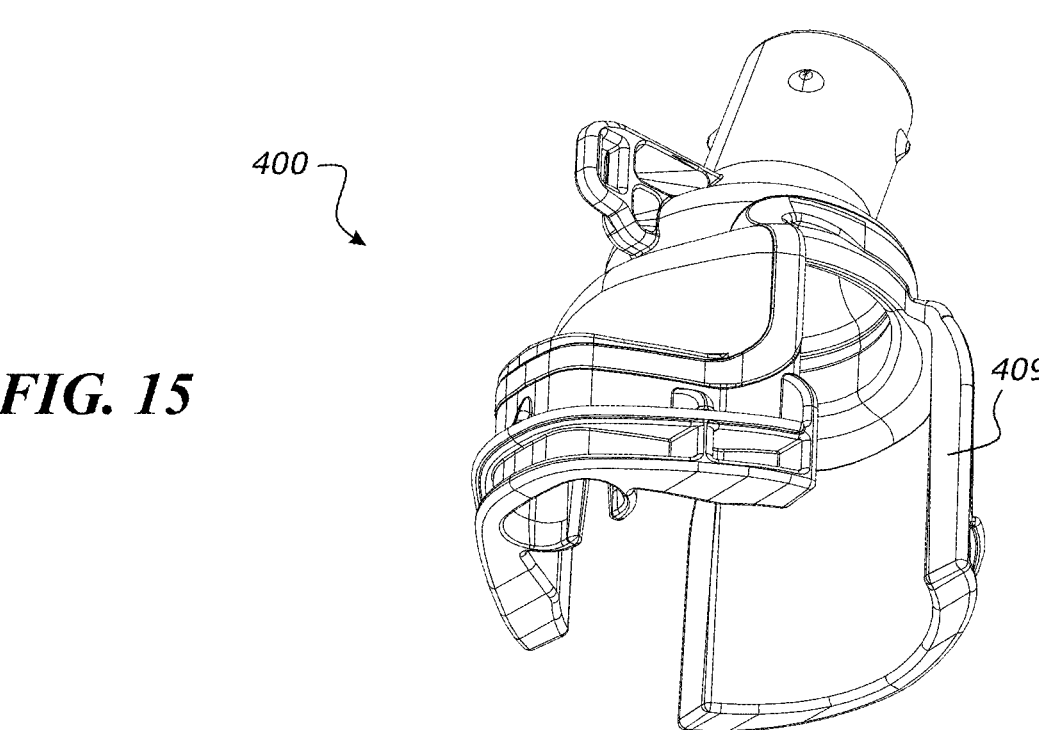
FIG. 15 is a perspective view from below of the outer body of FIG. 14.
Figure 16:
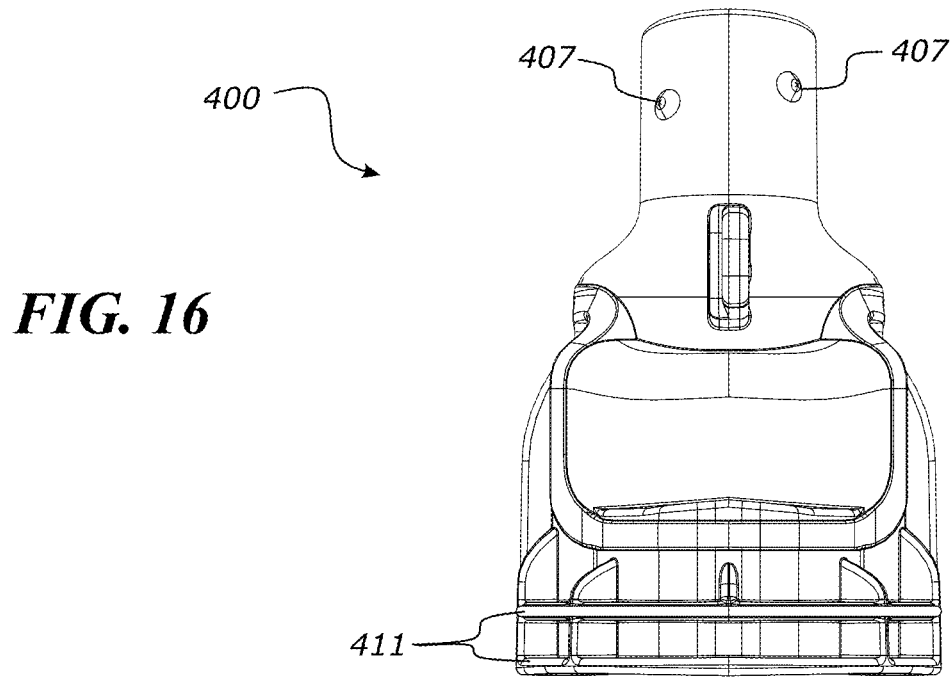
FIG. 16 is a front view of the outer body of FIG. 14.
Figure 17:
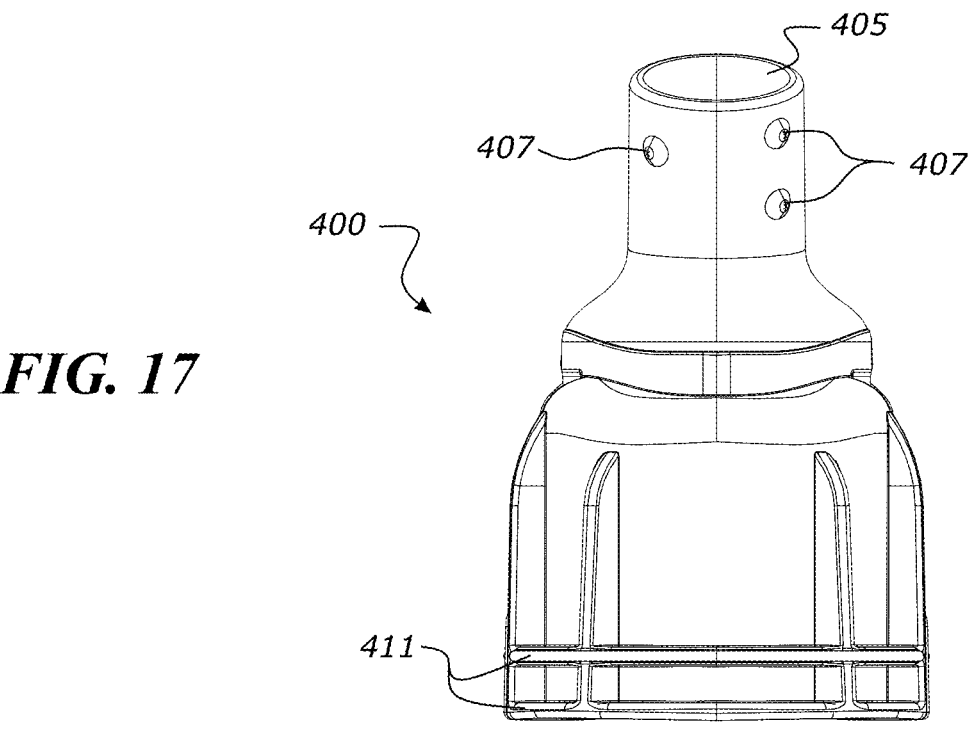
FIG. 17 is a back view of the outer body of FIG. 14.
Figure 18:
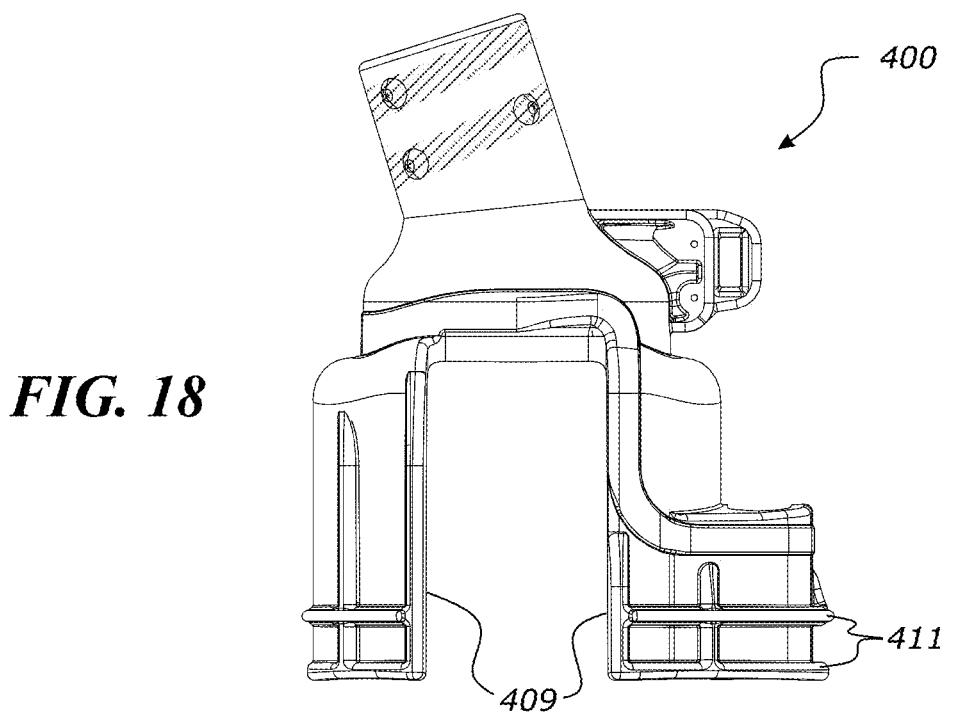
FIG. 18 is a side view of the outer body of FIG. 14.
Figure 19:
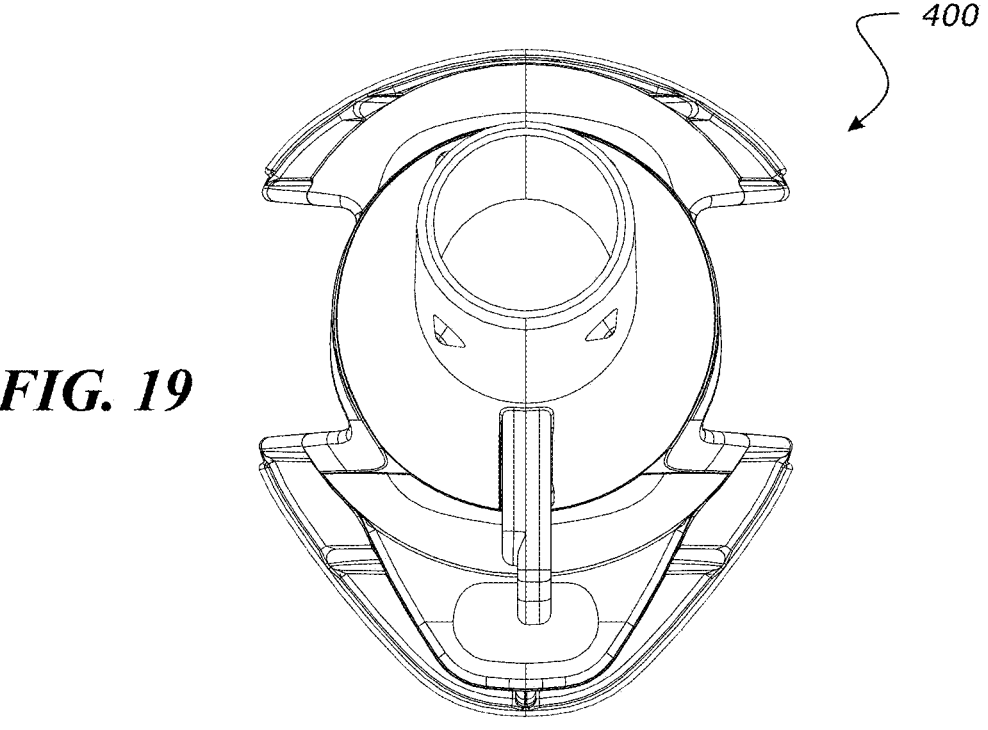
FIG. 19 is a top view of the outer body of FIG. 14.
Figure 20:
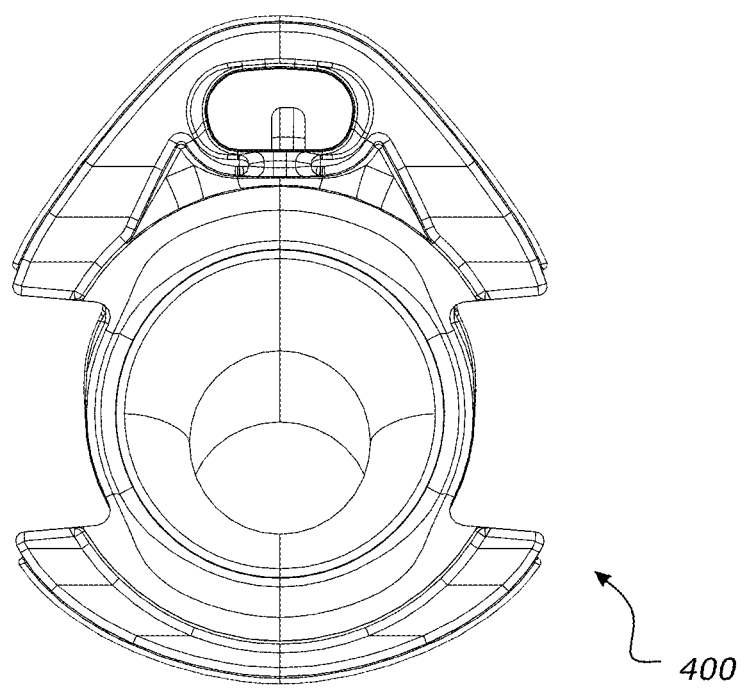
FIG. 20 is a bottom view of the outer body of FIG. 14.

With reference to FIG. 14, the tube connection portion extends at an angle of more than about 0° and less than about 90° from a longitudinal axis of the body. The angle is more than about 5° and less than about 60°, more than about 10° and less than about 40°, or more than about 15° and less than about 20°. The tube connection portion extends at an angle of more than about 0° and less than about 90° from a longitudinal axis of one of the electrical sub-assembly 500.

The outer body 400 has an outer wall that surrounds a significant portion of the inner body 200. When the connector 100 is connected to the second connector 800 of the device, the outer wall additionally surrounds the second connector 800. The outer wall can have cut-out sections to allow for passage of the bridges on the inner body 200 when assembling the inner body 200 and body together.

The width of the cut-outs would preferably match the distance between the tips of the alignment protrusions 209 located on each bridge 205 of the inner body 200. When assembled, the protrusions would contact the cut-out on each side to ensure the correct angular alignment between the inner body 200 and the outer body 400.

Electrical Pins

The connector 100 has an electrical sub-assembly 500. The electrical sub-assembly 500 has a body 501 and electrical pins (contacts) 503 extending outwardly from the body 501. The electrical sub-assembly body 501 is formed from a non-conductive material. The electrical sub-assembly 500 is received by a receptacle of the outer body 400. Once the electrical sub-assembly 500 is assembled with the outer body 400, the upper ends of the electrical pins are soldered onto the exposed electrical contacts of the conduit.

The lower ends of the electrical pins 503 pass through the receptacle and into an exposed recess at the base of the outer body. This section forms the electrical connector portion of the connector 100. When assembled with the device outlet, a protruding electrical connector on the device inserts into the recessed electrical connector on the connector, with the electrical pins 503 inserting into holes in the protruding electrical connector.

The outer body 400 can also include alignment or lead in features, which aid in aligning the electrical connections of the device and the connector 100. The alignment or lead in features could be in the form of a tapered terminal end of the receptacle, such that the connector 100 is urged into the correct angular alignment with the second connector 800 as the user pushes the two components together.

The body 501 can have a spacing portion that is designed to abut an upper surface of the outer body 400 around the receptacle. This serves to locate the electrical sub-assembly 500 at the correct height prior to soldering. The base of the body can additionally have one or more protrusions that correspond to a recess inside the receptacle. When assembling the electrical sub-assembly 500 with the outer body 400, the protrusion clips into the recess in order to hold the electrical sub-assembly 500 in place for the soldering and further overmoulding processes.

The electrical sub-assembly 500 can have a retention feature in the form of a tab that extends horizontally from the upper portion of the overmould. The retention feature would insert into a complementary recess on the outer body 400 to create a more secure fit between the outer body 400 and the electrical sub-assembly 500 prior to being further overmoulded.

Intermediate Shell

Once the electrical insert 500 has been assembled with the outer body 400 and soldered to the conduit's electrical contacts, an intermediate shell 600 is applied to the outer body 400. The intermediate shell 600 is between the outer body 400, and the cover 700, when the connector 100 is fully assembled.

The intermediate shell 600 covers the electrical sub-assembly 500, the end portion of the conduit 300, and the soldered electrical contacts. This serves to protect the electrical connection, as well as to retain the assembled electrical sub-assembly 500 and conduit 300 with the outer body 400. The intermediate shell 600 also acts as another layer of protection in pneumatically sealing the electrical connection from gases, such as oxygen rich gas that leaks from the device or other devices.

The outer body 400 and electrical sub-assembly 500 can be assembled with the intermediate shell 600 prior to assembling the outer body 400 with the inner body 200. The material used for the intermediate shell 600 would be similar to that used for the outer body 400, or a compatible material, such that the intermediate shell 600 and the outer body 400 bind together. The materials used for the intermediate shell 600 and the outer body 400 would in turn be similar to, or compatible with, the material used for the conduit 300 in order to facilitate bonding between the conduit 300 and the intermediate shell 600 and the outer body 400.

The material of the outer body 400 and the intermediate shell 600 can be co-moulded or over-moulded without the moulding process of one of the components affecting the moulding process of the other component. For example, both materials have a melting temperature that does not affect the other component. In particular, moulding the intermediate shell 600 over the outer body 400 does not cause the outer body 400 to melt or deform. In addition, the intermediate shell 600 and the outer body 400 bind together.

As mentioned above, having a separate inner body 200 and body in this scenario is beneficial, as one material may be used for the inner body 200 to meet the required mechanical performances, while a second material is used for the outer body 400 to allow for bonding with the overmould.

The outer body 400 may have raised features around the edge of the section that is being overmoulded with the intermediate shell 600. This makes it easier for the manufacturing tools to create a proper seal during the overmoulding process, thereby reducing the chance of defects in the overmould, such as flash.

When connecting the connector 100 to the second connector 800, the pneumatic seal, i.e. the wiper seal of the inner body 200 sealing against the device outlet, is preferably created before the electrical connection between the electrical pins 503 of the connector 100 and the electrical connector of the device.

In the embodiment shown, the intermediate shell 600 is overmoulded to, or co-moulded with, the outer body 400.

Elastomeric Outer Cover

As described above, the inner body 200 and outer body 400 defines a gases pathway for gas to flow, for example, from a respiratory device to a patient interface. The accompanying figures shows details of the inner body 200 retention mechanism with an actuation feature. In one alternative embodiment, the outer body 400 may have a retention mechanism with an actuation feature.

In another alternative embodiment, the connector may have a single body (without separate inner and outer bodies). That single body may have a retention mechanism with an actuation feature.

The actuation feature is manually operable. According to the embodiment described herein, the actuation feature is the actuation portion of the lever. In alternative embodiments, the actuation feature may be a button, switch, or part of the body that moves in response to being manually operated.

A cover 700 may be provided to cover the connector 100 to surround the various components. The cover 700 is formed as a sleeve 701 having a first opening 701 and a second opening 703. The first opening is smaller than the second opening. The shape of the sleeve generally corresponds to the shape of the other components of the connector, including the outer body 400 and the intermediate shell 600. The cover 700 is formed from an elastomeric material. The cover 700 is flexible and resilient. The cover 700 also has a higher coefficient of friction compared to the coefficient of friction of the outer body.

The cover 700 extends over the actuation feature. Although the flexible cover 700 extends over the actuation feature, it also allows the actuation feature to be manually operated by the user. The cover 700 also allows the finger to deflect with minimal force and does not affect the actuation of the actuation feature.

The cover 700 could be slid onto the conduit 300 prior to assembly in order to be slid onto the connector 100 after the various components have been assembled. The cover 700 is friction or interference fitted with the outer body 400. The cover 700 comprises semi-annular recesses 705 near the base of the inside of the cover 700, which complement semi-annular protrusions on the base of the outside of the outer body 400.

In an alternative embodiment, the recesses may have other shapes. For example, the recess could be completely annular. The interaction between the recesses 705 and protrusions serves to retain the cover 700 on the outer body 400. Additionally or alternatively, the cover 700 and the outer body 400 could also be friction and/or interference fitted together.

The cover 700 provides a uniform outer surface. The cover 700 also protects various components of the connector 100. The outer body 400 and intermediate shell 600 can be shaped to be complementary to an inner surface of the cover 700. This supports the cover 700 such that the assembled connector 100 has a solid feel to it, as opposed to having hollow sections. The intermediate shell 600 and/or the outer body 400 can achieve this shape through a series of ribs, such that the intermediate shell 600 and/or the outer body 400 can achieve the desired shape without using an excessive amount of material.

When actuating the levers 203, the cover 700 acts as an intermediary surface for applying pressure to the upper portion of the levers 203. This provides a softer and more rounded surface for the user to interact with. The cover 700 could have an indicator of where the user needs to apply pressure in order to actuate the levers 203.

The indicator could take the form of a surface feature that is identifiable by touch and/or by sight. The indicator could have a thickened cross section, which would provide a more comfortable feel to the user when actuating the tabs. In the embodiment shown, the cover 700 has a thickened portion 707 that corresponds to the actuation portion 203A. The thickened portion 707 has an external surface feature 709. The cover 700 has a thinned portion 711 connecting the thickened portion to the rest of the cover 700. The thinned portion 711 allows adjacent portions of the cover 700 to move, when actuated. In particular, the thinned portion 711 allows the thickened portion(s) to move inwardly, or towards the centre of the connector 100, when actuated. The cover 700 can have a portion of thinner material adjacent to the indicator, thereby allowing the said section of material to more easily fold in on itself when the tabs are actuated.

As the cover 700 is made from an elastomeric material, the material of the cover 700 allows the cover 700 to both move from its at rest shape to an actuated shape and then return to the at rest shape.

The cover 700 may have a base 713 with a thickened shoulder 715. The shoulder 715 provides a surface for the user to push on when attaching the connector to the second connector 800. The thickened portion, in combination with being formed form an elastomeric material, additionally may provide an inwardly directed force around the perimeter of the connector 100, in particular around the retention portion 203B of the levers 203. In other words, the cover 700 may be pre-formed to provide for a direction of inward bias. Alternatively, the cover 700 may be formed so as to be slightly smaller than the connector 100, such that once the cover 700 is in-situ, a 'stretch' of the cover can be achieved to retain the cover in place upon the connector 1000. The above may increase the force retaining the protrusions within the complementary recesses of the second connector 800.

Figure 31A:
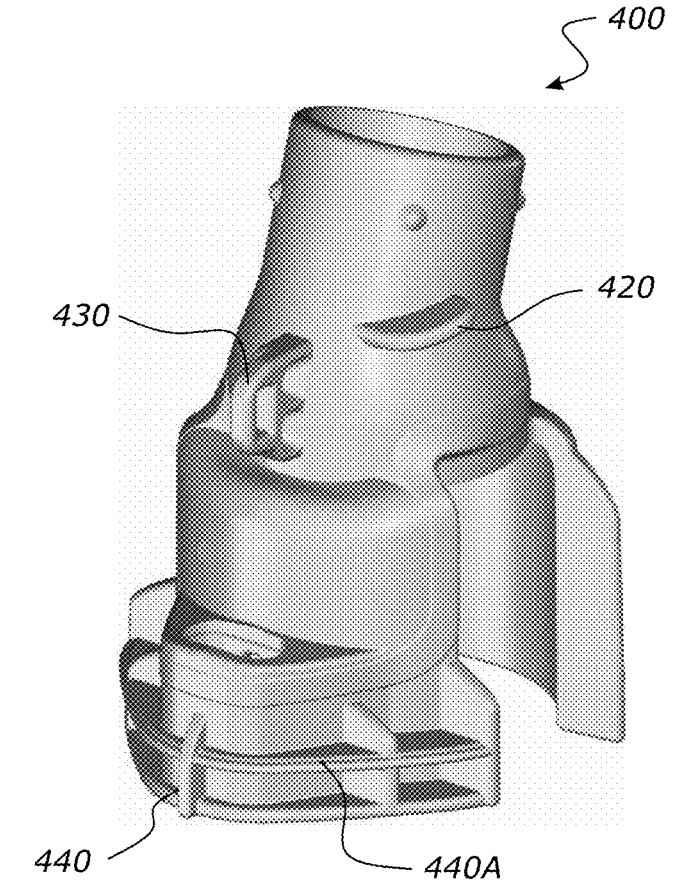
FIG. 31A shows a perspective view of an alternative embodiment of an outer body of a connector as described herein.

FIGS. 31A and B show alignment features in the form of ribs 440. That may correspond to recesses in the thickened portions outlined above.

The cover 700 has a number of features that complement features of the outer body 400. In particular, the cover 700 and the outer body 400 have complementary features (e.g. ribs 440 and their corresponding recesses in the thickened portions of the cover 700) to key those components together and prevent rotation or pivoting of the cover 700 relative to the outer body 400. In particular, the outer body 400 has ribs 440 and the cover 700 has complementary recesses.

Figure 31B:
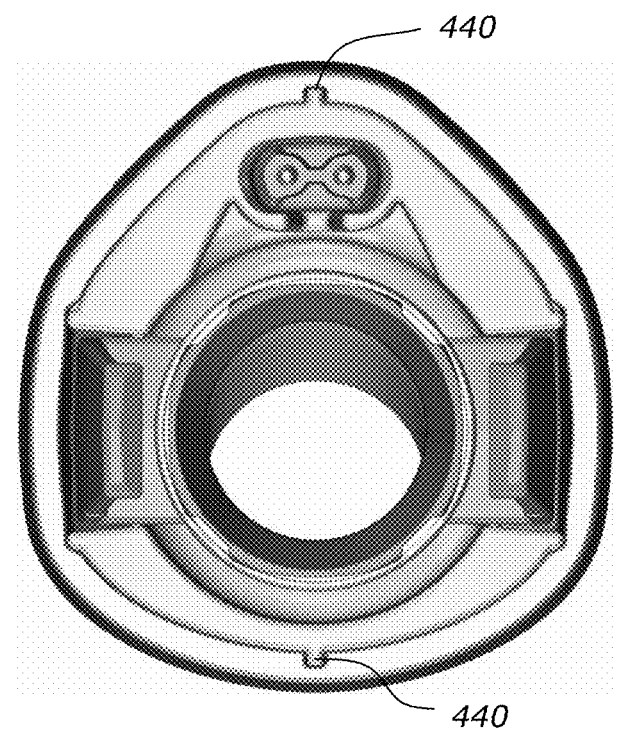
FIG. 31B shows a bottom view of an alternative embodiment of an outer body of a connector as described herein. A cover (such as the cover shown in FIG. 1B), and an electrical sub-assembly (such as electrical sub-assembly shown in FIGS. 2 and 25) are also shown.

Some of ribs 440 extend in a direction that is transverse to possible direction of rotation. In particular, some of the ribs extend vertically (or substantially parallel to a central axis of the connector 100) to prevent, or at least substantially inhibit, rotation in a perpendicular direction, as shown by ribs 440 in FIGS. 31A and 31B. The other ribs are semi-circular ribs 440A that nest in complementary recesses in the cover. Again, these ribs prevent, or at least substantially inhibit, rotation of the cover 700 relative to the outer body 400, and may aid in retention of the cover on the outer body.

In certain embodiments the feature to key the cover and outer body 400 together and prevent rotation or pivoting of the cover 700 relative to the outer body 400 comprises a non-circular shape of the outer body 400 and cover 700. The outer body 400 and/or the intermediate shell 600 has one or more ribs to support the cover 700. The outer body 400 has an electrical sub-assembly for electrical connection. The body has an overmould to pneumatically seal about the electrical connection.

As described, the material of the outer body 400 is the same as, or is compatible with the material of the conduit 300. That is, the material of the outer body and the conduit can be co-moulded or over-moulded without the moulding process of one of the components affecting the moulding process of the other component. For example, both materials have a melting temperature that does not affect the other component. In particular, moulding the outer body over the conduit does not cause the conduit to melt or deform. In addition, the outer body and the conduit bind together.

In some embodiments, the connector 100 may be provided in combination with the conduit 300. For example, the outer body 400 may be overmoulded over the conduit 300. The intermediate shell 600 may also be overmoulded over the conduit 300, the outer body 400, or both the conduit 300 and the outer body 400. In the embodiment shown, the intermediate shell 600 is also overmoulded over the electrical sub-assembly 500.

In some embodiments, the inner body 200, the outer body 400, and the cover 700 may be made from the same material. In other embodiments, the inner body 200, the outer body 400, and the cover 700 may be made from different materials.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein the term "(s)" following a noun means the plural and/or singular form of that noun.

As used herein the term "and/or" means "and" or "or", or where the context allows both.

Where the terminology "configured to" is used herein, that terminology could alternatively be replaced with "arranged to" or "adapted to".

Where, in the foregoing description reference has been made to integers or components having known equivalents thereof, those integers are herein incorporated as if individually set forth.

The disclosure may also be said broadly to consist in the parts, elements and features referred to or indicated in the specification of the application, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Certain features, aspects and advantages of some configurations of the present disclosure have been described with reference to use of the gas humidification system with a respiratory therapy system. However, certain features, aspects and advantages of the use of the gas humidification system as described may be advantageously used with other therapeutic or non-therapeutic systems requiring the humidification of gases or even non-humidified systems. Certain features, aspects and advantages of the methods and apparatus of the present disclosure may be equally applied to connectors and usage with other systems requiring alternative connectors.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Features from any of the configurations described above may be combined with each other and/or a respiratory support system or humidifier or other components or devices forming a part of a respiratory therapy system or a system for delivery for gases to a patient may comprise one or more of the above described configurations. Moreover, not all of the features, aspects and advantages are necessarily required to practice the present disclosure. Accordingly, the scope of the present disclosure is intended to be defined only by the claims that follow.

The invention claimed is:

1. A connector for a component of a medical breathing circuit, the connector comprising:

an inner body and an outer body, the inner body and the outer body being separate components, the inner body having a retention mechanism configured to engage another connector;

an outer body configured to at least partly surround the inner body, the outer body having a tube engagement mechanism;

wherein the connector further comprises at least one electrical contact and the outer body comprises an overmould configured to form a pneumatic seal about the at least one electrical contact;

wherein at least part of the inner body comprises a first material and at least part of the outer body comprises a second material, and wherein the first material is stiffer than the second material;

wherein the retention mechanism of the inner body comprises a flexing region provided by a bridge, wherein the flexing region comprises the first material; and wherein the bridge is arranged between an actuation portion and the retention mechanism.

2. The connector of claim 1, wherein the inner body further comprises a sealing mechanism configured to provide a seal between the inner body and another connector.

3. The connector of claim 1, wherein the retention mechanism comprises at least one lever that is movable relative to the inner body about the flexing region.

4. The connector of claim 3, wherein the at least one lever has a retention portion on one portion of the flexing region and an actuation portion on another portion of the flexing region.

5. The connector of claim 4, wherein the at least one lever comprises a first lever and a second lever, wherein a distance between the retention mechanism of the first lever and the second lever in a disengaged configuration is equal to or less than the distance in an engaged configuration.

6. The connector of claim 1, wherein the outer body has cut-outs to allow a portion of the inner body to sit within the outer body and a portion of the inner body to sit outside the outer body.

7. The connector of claim 6, wherein the portion of the inner body to sit outside the outer body is the retention mechanism.

8. The connector of claim 1, wherein the bridge has features to align the bridge with the outer body.

9. The connector of claim 1, wherein the bridge comprises a strengthening feature.

10. The connector of claim 1, wherein the first material has a higher Young's modulus than the second material.

11. The connector of claim 1, further comprising an inner body and outer body sealing mechanism configured to seal the inner body and the outer body together, and an inner body and outer body retention mechanism configured to retain the inner body and the outer body together, the inner body and outer body sealing mechanism and the inner body and outer body retention mechanism being separate mechanisms.

12. The connector of claim 11, wherein a terminal end of the inner body extends beyond an end of the outer body.

13. The connector of claim 12, wherein the terminal end has a greater diameter than a remainder of the inner body.

14. The connector of claim 13, wherein the inner body comprises a wall tapering outwardly towards the terminal end.

15. The connector of claim 14, wherein a diameter of an inner wall of the inner body at the terminal end is greater than the diameter of a remainder of the inner wall.

\* \* \* \* \*